United States Patent
Suenaga et al.

(10) Patent No.: US 11,529,302 B2
(45) Date of Patent: Dec. 20, 2022

(54) COMPOSITION, ARTIFICIAL NAIL COMPOSITION, NAIL DECORATION MATERIAL, ARTIFICIAL NAIL, STORED CONTAINER, IMAGE FORMING APPARATUS, AND IMAGE FORMING METHOD

(71) Applicant: RICOH COMPANY, LTD., Tokyo (JP)

(72) Inventors: Takenori Suenaga, Kanagawa (JP); Masahide Kobayashi, Kanagawa (JP); Mitsunobu Morita, Shizuoka (JP); Takashi Okada, Kanagawa (JP); Soh Noguchi, Kanagawa (JP); Tatsuki Yamaguchi, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 116 days.

(21) Appl. No.: 16/441,844

(22) Filed: Jun. 14, 2019

(65) Prior Publication Data
US 2020/0038310 A1 Feb. 6, 2020

(30) Foreign Application Priority Data

Jul. 31, 2018 (JP) .............. JP2018-143431
Feb. 4, 2019 (JP) .............. JP2019-017699

(51) Int. Cl.
*A61K 8/87* (2006.01)
*A61Q 3/02* (2006.01)

(52) U.S. Cl.
CPC . *A61K 8/87* (2013.01); *A61Q 3/02* (2013.01)

(58) Field of Classification Search
CPC ............. A61K 8/87; A45D 31/00; A61Q 3/02
See application file for complete search history.

(56) References Cited

U.S. PATENT DOCUMENTS

| | | |
|---|---|---|
| 9,267,043 B2 | 2/2016 | Morita et al. |
| 9,796,862 B2 | 10/2017 | Morita et al. |
| 10,174,215 B2 | 1/2019 | Morita et al. |
| 2010/0053290 A1 | 3/2010 | Nakamura |
| 2013/0144057 A1 | 6/2013 | Morita |
| 2014/0363634 A1 | 12/2014 | Morita et al. |
| 2015/0173483 A1* | 6/2015 | Raouf ............... A45D 29/001 132/200 |
| 2016/0023984 A1 | 1/2016 | Morita et al. |
| 2016/0075894 A1 | 3/2016 | Noguchi et al. |
| 2016/0340458 A1* | 11/2016 | Hiraoka ............... C09D 133/14 |
| 2017/0137644 A1 | 5/2017 | Morita et al. |
| 2018/0127607 A1 | 5/2018 | Morita et al. |

FOREIGN PATENT DOCUMENTS

| | | |
|---|---|---|
| JP | 2006-335988 | 12/2006 |
| JP | 2010-059244 | 3/2010 |
| JP | 5240939 | 4/2013 |
| JP | 2015-013980 | 1/2015 |
| JP | 2015-189668 | 11/2015 |
| JP | 2015-209390 | 11/2015 |
| JP | 2016-141634 | 8/2016 |
| JP | 2016-220733 | 12/2016 |
| JP | 2018-080321 | 5/2018 |
| WO | WO 2016/096632 | * 6/2016 |

* cited by examiner

OTHER PUBLICATIONS

Scifinder, Esacure One, (accessed Jul. 10, 2020), pp. 1-2 (Year: 2020).*

*Primary Examiner* — Andrew S Rosenthal
*Assistant Examiner* — Lyndsey M Beckhardt
(74) *Attorney, Agent, or Firm* — Grüneberg and Myers PLLC

(57) ABSTRACT

Provided is a composition including: an acrylamide compound represented by general formula (1) below; urethane (meth)acrylate having a SI value of 3 or less in a skin sensitization test; and a polymerization initiator having a molecular weight of 800 or greater,

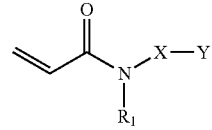

General formula (1)

where in general formula (1), $R_1$ represents an alkyl group containing 1 through 6 carbon atoms, X represents an alkylene group containing 1 through 6 carbon atoms, and Y represents any one selected from the group consisting of general formula (2) below and general formula (3) below,

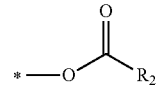

General formula (2)

where in general formula (2), $R_2$ represents an alkyl group containing 1 through 10 carbon atoms, and * represents a binding site with X above,

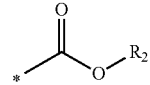

General formula (3)

where in general formula (3), $R_2$ represents an alkyl group containing 1 through 10 carbon atoms, and * represents a binding site with X above.

19 Claims, 2 Drawing Sheets

COMPOSITION, ARTIFICIAL NAIL COMPOSITION, NAIL DECORATION MATERIAL, ARTIFICIAL NAIL, STORED CONTAINER, IMAGE FORMING APPARATUS, AND IMAGE FORMING METHOD

CROSS-REFERENCE TO RELATED APPLICATIONS

The present application claims priority under 35 U.S.C. § 119 to Japanese Patent Application No. 2018-143431 filed Jul. 31, 2018 and Japanese Patent Application No. 2019-017699 filed Feb. 4, 2019.

The contents of which are incorporated herein by reference in their entirety.

BACKGROUND OF THE INVENTION

Field of the Invention

The present disclosure relates to a composition, an artificial nail composition, a nail decoration material, an artificial nail, a stored container, an image forming apparatus, and an image forming method.

Description of the Related Art

Gel nail has been known as a nail decorating method. Gel nail is a nail material that has fluidity and photopolymerization reactivity of curing when irradiated with ultraviolet rays or visible light.

As such gel nail, for example, there have been proposed artificial nail compositions containing a urethane-based resin, a monomer, and a polymerization initiator (for example, see Japanese Unexamined Patent Application Publication No. 2015-209390, Japanese Patent No. 5240939, Japanese Unexamined Patent Application Publication No. 2015-189668, and Japanese Unexamined Patent Application Publication No. 2016-141634).

SUMMARY OF THE INVENTION

According to one aspect of the present disclosure, a composition contains an acrylamide compound represented by general formula (1) below, urethane (meth)acrylate having a SI value of 3 or less in a skin sensitization test, and a polymerization initiator having a molecular weight of 800 or greater.

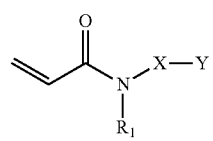

General formula (1)

In general formula (1), $R_1$ represents an alkyl group containing 1 through 6 carbon atoms, X represents an alkylene group containing 1 through 6 carbon atoms, and Y represents any one selected from the group consisting of general formula (2) below and general formula (3) below.

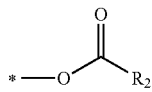

General formula (2)

In general formula (2), $R_2$ represents an alkyl group containing 1 through 10 carbon atoms, and * represents the binding site with X mentioned above.

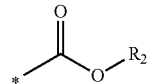

General formula (3)

In general formula (3), $R_2$ represents an alkyl group containing 1 through 10 carbon atoms, and * represents the binding site with X mentioned above.

DESCRIPTION OF THE EMBODIMENTS (Composition)

Figure 1:
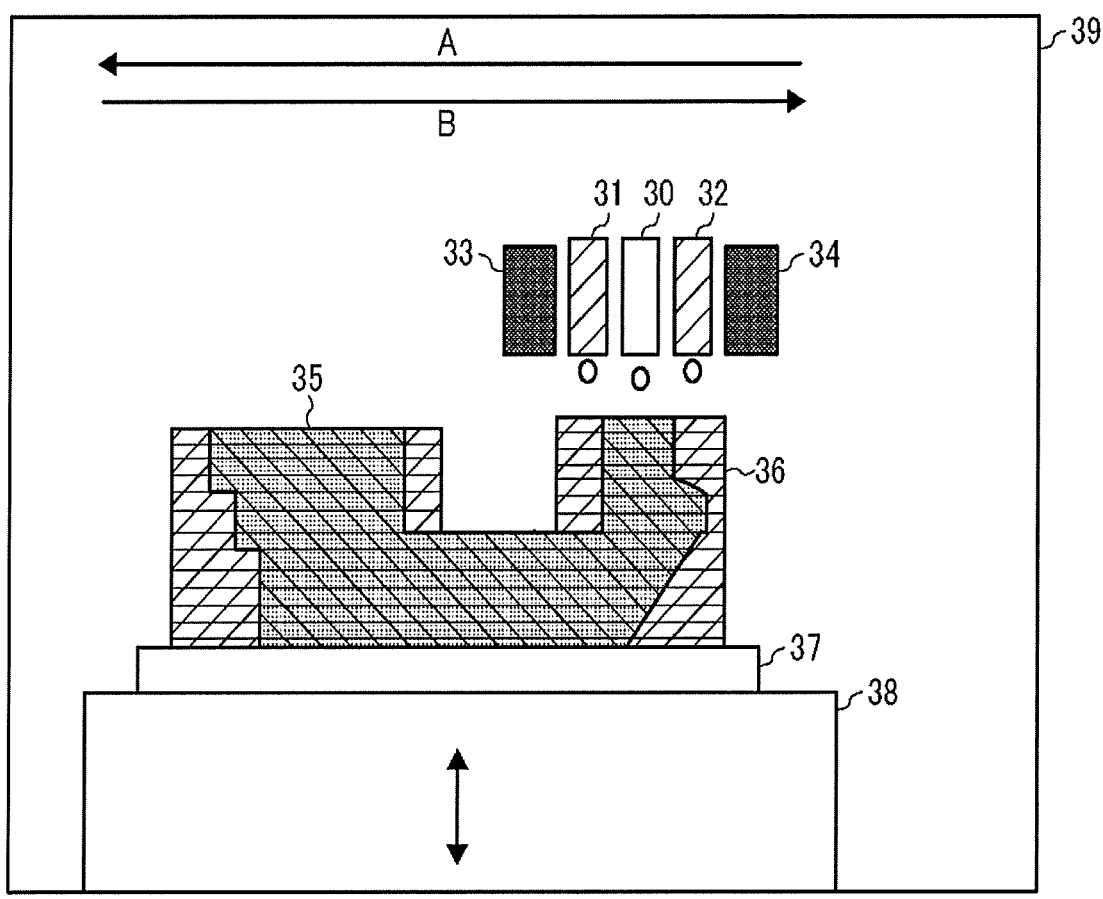
FIG. 1 is a schematic view illustrating an example of an image forming apparatus (three-dimensional stereoscopic image forming apparatus)
Figure 2A:
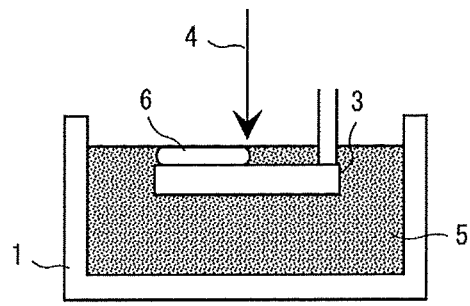
FIG. 2A is a schematic view illustrating an example of a method for forming a three-dimensional object using a composition.
Figure 2B:
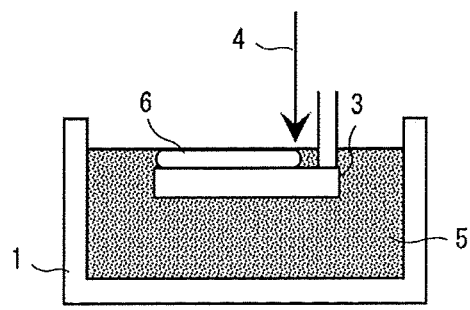
FIG. 2B is a schematic view illustrating an example of a method for forming a three-dimensional object using a composition.
Figure 2C:
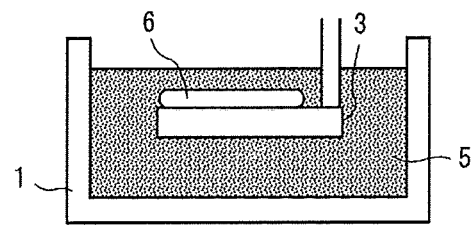
FIG. 2C is a schematic view illustrating an example of a method for forming a three-dimensional object using a composition.
Figure 2D:
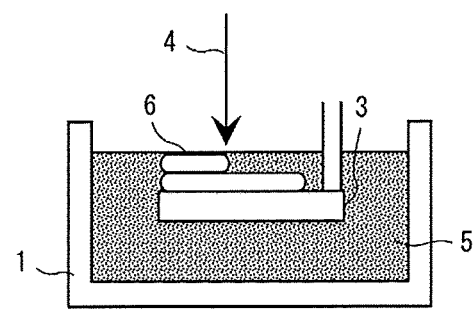
FIG. 2D is a schematic view illustrating an example of a method for forming a three-dimensional object using a composition.

A composition of the present disclosure contains an acrylamide compound represented by general formula (1) below, urethane (meth)acrylate having a SI value of 3 or less in a skin sensitization test, and a polymerization initiator having a molecular weight of 800 or greater.

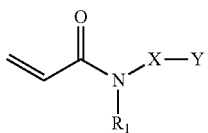

General formula (1)

In general formula (1), $R_1$ represents an alkyl group containing 1 through 6 carbon atoms, X represents an alkylene group containing 1 through 6 carbon atoms, and Y represents any one selected from the group consisting of general formula (2) below and general formula (3) below.

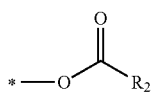

General formula (2)

In general formula (2), $R_2$ represents an alkyl group containing 1 through 10 carbon atoms, and * represents the binding site with X mentioned above.

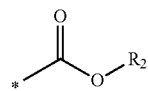

General formula (3)

In general formula (3), $R_2$ represents an alkyl group containing 1 through 10 carbon atoms, and * represents the binding site with X mentioned above.

The present disclosure has an object to provide a composition that can be reduced in odor and can provide a cured product safe in terms of skin sensitizing potential.

The present disclosure can provide a composition that can be reduced in odor and can provide a cured product safe in terms of skin sensitizing potential.

Being safe in terms of skin sensitizing potential means that the SI (Stimulation Index) value indicating the degree of sensitizing potential is 3 or less in a skin sensitization test by LLNA method.

The "LLNA method" is a skin sensitization test stipulated as OECD test guidelines. According to this method, the sensitizing potential is judged as non-problematic when the Stimulation Index (SI) value indicating the degree of skin sensitizing potential is 3 or less, as disclosed in documents (for example, the September 2005 issue of "Functional Materials", Vol. 25, No. 9, P55).

The composition of the present disclosure is based on the following finding. The existing techniques have problems in terms of, for example, odor, skin irritation, and skin sensitizing potential due to monomers and polymerization initiators. Particularly, most (meth)acrylic acid ester compounds that are easily available at low prices have a high toxicity in terms of skin sensitizing potential of causing allergies when touching skin. The existing techniques have not presented solutions to this problem.

By containing the acrylamide compound represented by general formula (1) above, the urethane (meth)acrylate having a SI value of 3 or less in a skin sensitization test, and the polymerization initiator having a molecular weight of 800 or greater, the composition of the present disclosure is suitable as an artificial nail composition, can be reduced in odor, and can provide a cured product safe in terms of skin sensitizing potential.

In view of the nature of use of artificial nail compositions, which are used in actual contact with human nails that may be exposed to water or shocks in daily life, what matters is that artificial nail compositions have close adhesiveness. Moreover, in view of the nature of artificial nail compositions that are brought into direct contact with human bodies, what matters is that artificial nail compositions have a SI value of 3 or less for safety in terms of skin-sensitizing potential. Hence, the present disclosure uses urethane (meth)acrylate having a SI value of 3 or less, which is excellent in close adhesiveness when cured and excellent in safety.

Further, in view of the nature of use, artificial nail compositions are susceptible to shocks and scratches, and need to have scratch resistance. Hence, it is suitable to blend a monomer different from the urethane (meth)acrylate. In view of safety in terms of skin sensitizing potential and odor during use, the present disclosure uses the acrylamide compound represented by general formula (1) above and the polymerization initiator having a molecular weight of 800 or greater.

The composition of the present disclosure is preferably a curable composition. Examples of the curable composition include thermosetting compositions and active-energy-ray-curable compositions. Active-energy-ray-curable compositions are more preferable.

As used herein, (meth)acrylic acid ester refers to acrylic acid ester or methacrylic acid ester, and (meth)acrylate refers to acrylate or methacrylate.

<Acrylamide Compound>

The acrylamide compound is represented by general formula (1) above.

$R_1$ in general formula (1) represents a straight-chain or branched alkyl group containing 1 through 6 carbon atoms.

Examples of the alkyl group containing 1 through 6 carbon atoms include a methyl group, an ethyl group, a propyl group, an isopropyl group, an n-butyl group, an s-butyl group, an isobutyl group, a t-butyl group, a pentyl group, a neopentyl group, and a hexyl group.

X in general formula (1) represents a straight-chain or branched alkylene group containing 1 through 6 carbon atoms.

Examples of the alkylene group containing 1 through 6 carbon atoms include a methylene group, an ethylene group, a propylene group, and a butylene group.

Y in general formula (1) represents any one selected from the group consisting of general formula (2) above and general formula (3) above.

$R_2$ in general formula (2) above represents a straight-chain or branched alkyl group containing 1 through 10 carbon atoms.

Examples of the alkyl group containing 1 through 10 carbon atoms include a methyl group, an ethyl group, a propyl group, an isopropyl group, an n-butyl group, an s-butyl group, an isobutyl group, a t-butyl group, a pentyl group, a neopentyl group, a hexyl group, a heptyl group, an octyl group, a nonyl group, and a decyl group.

The "*" symbol in general formula (2) represents the binding site with X mentioned above.

$R_2$ in general formula (3) above represents a straight-chain or branched alkyl group containing 1 through 10 carbon atoms.

Examples of the alkyl group containing 1 through 10 carbon atoms include a methyl group, an ethyl group, a propyl group, an isopropyl group, an n-butyl group, an s-butyl group, an isobutyl group, a t-butyl group, a pentyl group, a neopentyl group, a hexyl group, a heptyl group, an octyl group, a nonyl group, and a decyl group.

The "*" symbol in general formula (3) represents the binding site with X mentioned above.

$R_1$ in general formula (1) above represents a straight-chain or branched alkyl group containing 1 through 6 carbon atoms.

Examples of the alkyl group containing 1 through 6 carbon atoms include a methyl group, an ethyl group, a propyl group, an isopropyl group, an n-butyl group, an s-butyl group, an isobutyl group, a t-butyl group, a pentyl group, a neopentyl group, and a hexyl group.

X in general formula (1) above represents a straight-chain or branched alkylene group containing 1 through 6 carbon atoms.

Examples of the alkylene group containing 1 through 6 carbon atoms include a methylene group, an ethylene group, a propylene group, and a butylene group.

Y in general formula (1) represents any one selected from the group consisting of general formula (2) above and general formula (3) above.

$R_2$ in general formula (2) above represents a straight-chain or branched alkyl group containing 1 through 10 carbon atoms.

Examples of the alkyl group containing 1 through 10 carbon atoms include a methyl group, an ethyl group, a propyl group, an isopropyl group, an n-butyl group, an s-butyl group, an isobutyl group, a t-butyl group, a pentyl group, a neopentyl group, a hexyl group, a heptyl group, an octyl group, a nonyl group, and a decyl group.

The "*" symbol in general formula (2) above represents the binding site with X mentioned above.

$R_2$ in general formula (3) above represents a straight-chain or branched alkyl group containing 1 through 10 carbon atoms.

Examples of the alkyl group containing 1 through 10 carbon atoms include a methyl group, an ethyl group, a propyl group, an isopropyl group, an n-butyl group, an s-butyl group, an isobutyl group, a t-butyl group, a pentyl group, a neopentyl group, a hexyl group, a heptyl group, an octyl group, a nonyl group, and a decyl group.

The "*" symbol in general formula (3) represents the binding site with X mentioned above.

It is preferable that Y in general formula (1) representing the acrylamide compound having an ester structure be represented by general formula (3) above.

It is preferable that $R_2$ in general formula (3) above be an alkyl group containing 1 through 2 carbon atoms.

The acrylamide compound represented by general formula (1) is a monofunctional acyclic tertiary acrylamide having an ester structure at an end. Typically, low-molecular-weight tertiary acrylamide compounds have volatility and hence a strong odor unique to monomers, leading to discomfort during handling of curable compositions containing these compounds.

Hence, the tertiary acrylamide compound represented by general formula (1) above has an ester structure at an end. Hence, volatility reduction owing to the ester structure enables odor suppression. Moreover, it is considered that intermolecular interaction owing to the presence of the ester structure can improve curability.

There are many commercially available products of acrylamide compounds containing a polymerizable acrylamide group but free of an ester structure (e.g., N-acryloylmorpholine, N,N-dimethyl acrylamide, N,N-diethyl acrylamide, N-isopropyl acrylamide, N-(2-hydroxyethyl)acrylamide, N-(hydroxymethyl)acrylamide, N-(butoxymethyl) acrylamide, N-[3-(dimethylamino)propyl]acrylamide, N-(1,1-dimethyl-3-oxobutyl)acrylamide, and 2-acrylamide-2-methyl propane sulfonic acid). However, it is difficult to find products that satisfy all of the effects of the present disclosure. The present disclosure is based on a finding that the acrylamide compound represented by general formula (1) satisfies the effects of the present disclosure by having an ester structure having neutrality and an appropriate polarity.

Next, groups of example compounds a to h will be presented below as specific examples of the acrylamide compound represented by general formula (1) above. However, these example compounds are non-limiting examples.

The group of example compounds a includes groups of compounds a1 to a6 presented below. One of these compounds may be used alone or two or more of these compounds may be used in combination.

<<Group of Example Compounds a1>>

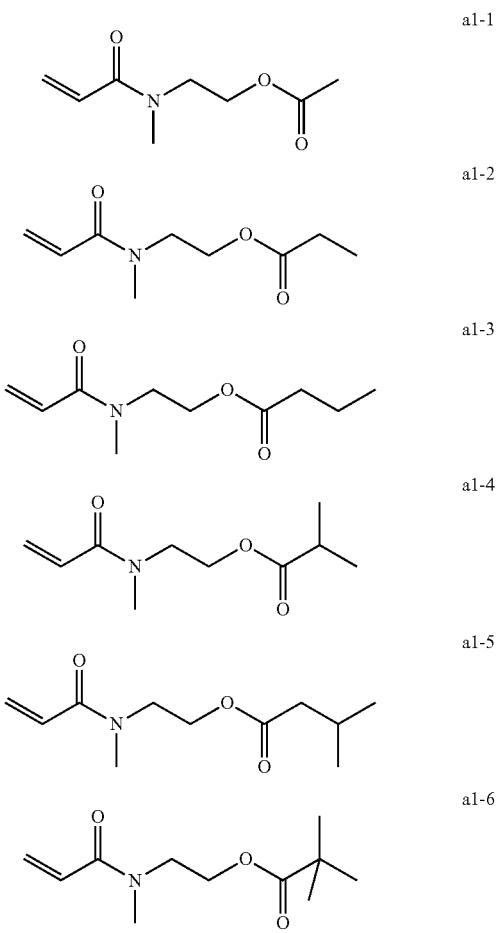

<<Group of Example Compounds a2>>

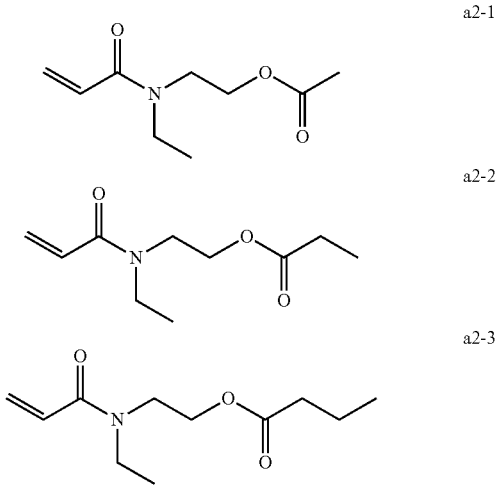

<<Group of Example Compounds a4>>
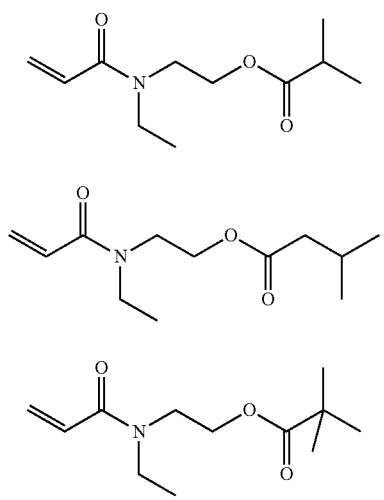
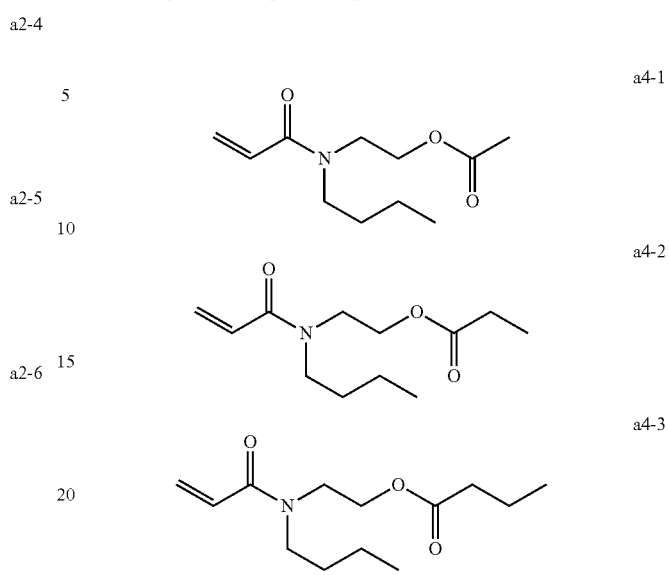
<<Group of Example Compounds a3>>
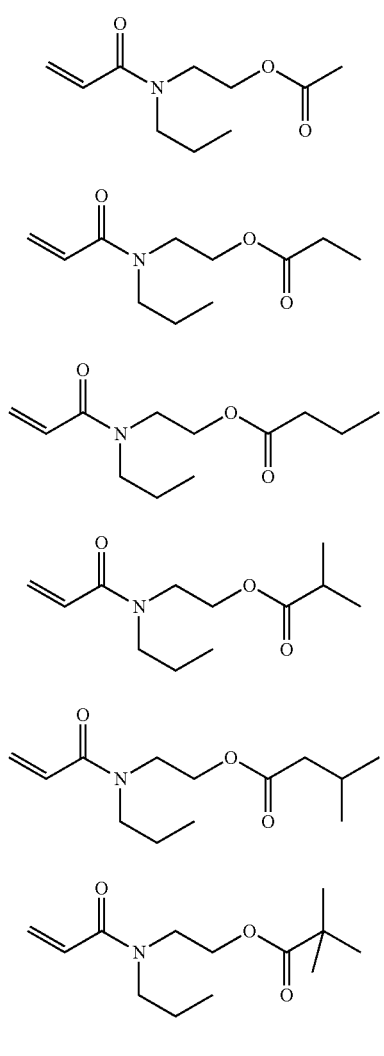
<<Group of Example Compounds a5>>
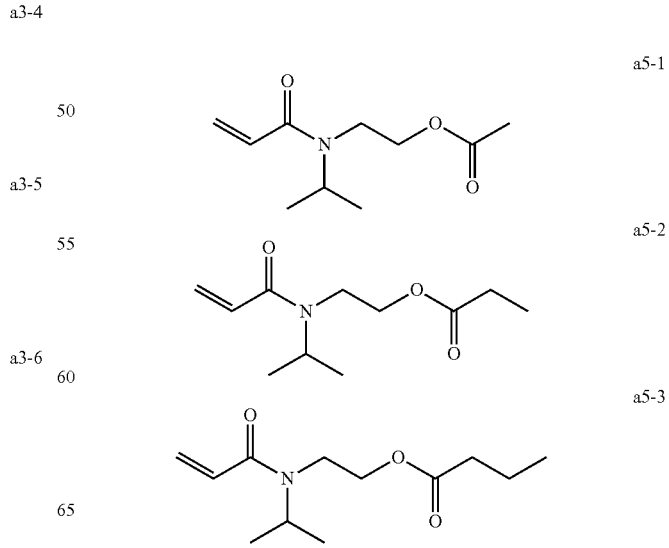

a5-4
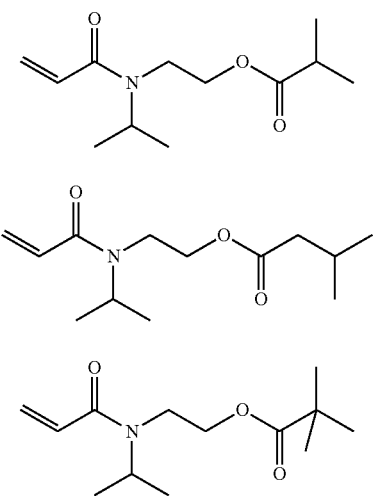
a5-5
a5-6
<<Group of Example Compounds a6>>
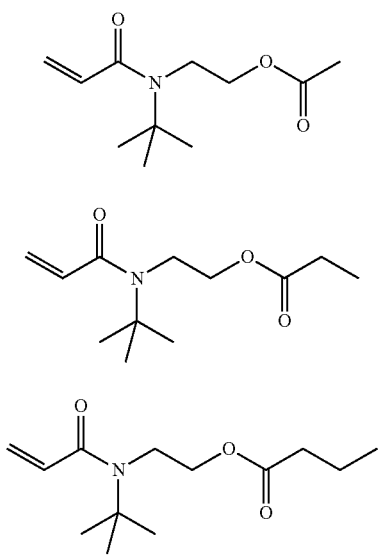
a6-1
a6-2
a6-3
a6-4
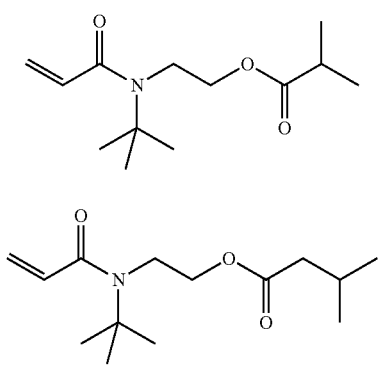
a6-5
a6-6
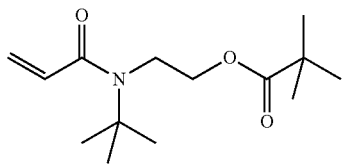
The group of example compounds b includes groups of compounds b1 to b6 presented below. One of these compounds may be used alone or two or more of these compounds may be used in combination.
<<Group of Example Compounds b1>>
b1-1
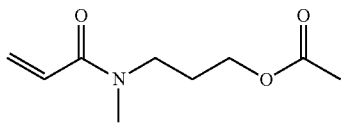
b1-2
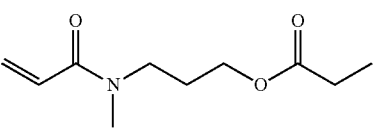
b1-3
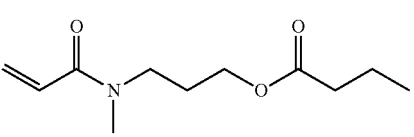
b1-4
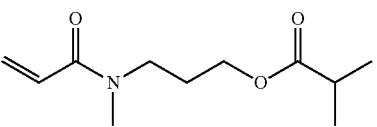
b1-5
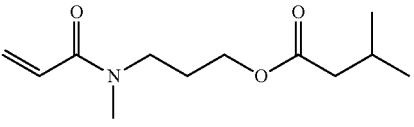
b1-6
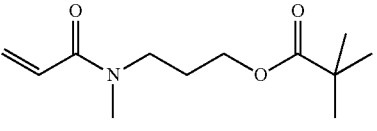
<<Group of Example Compounds b2>>
b2-1
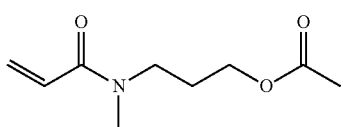
b2-2
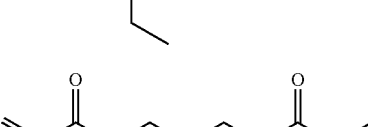

b2-3
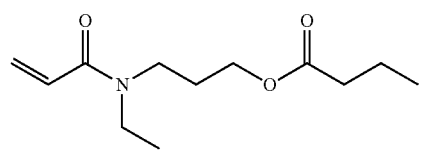
b2-4
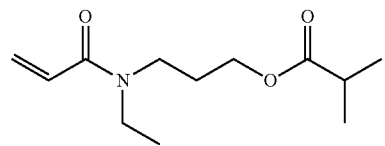
b2-5
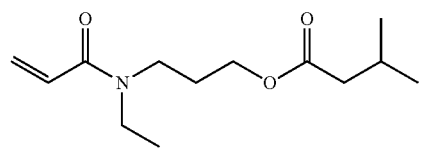
b2-6
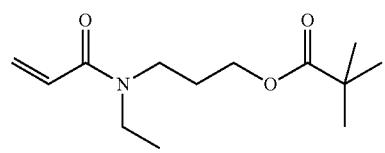
<<Group of Example Compounds b3>>
b3-1
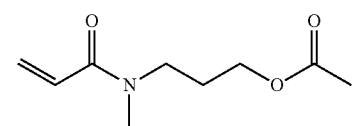
b3-2
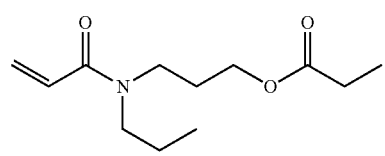
b3-3
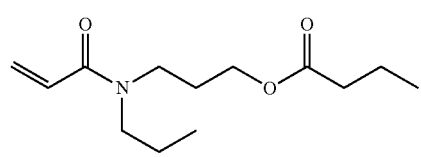
b3-4
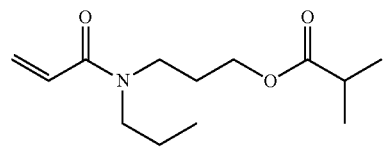
b3-5
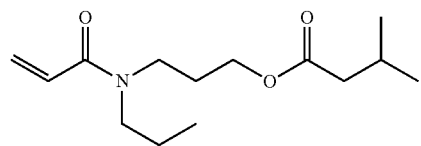
b3-6
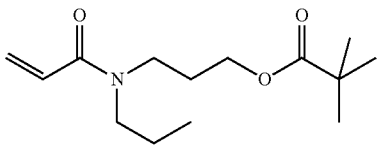
<<Group of Example Compounds b4>>
b4-1
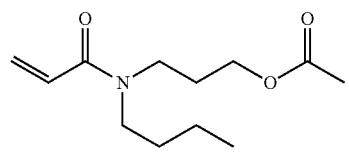
b4-2
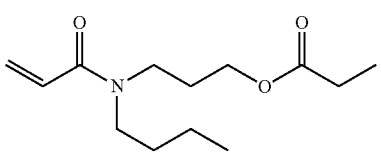
b4-3
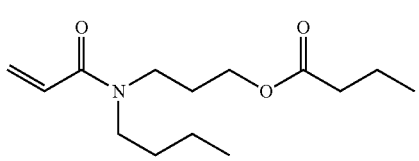
b4-4
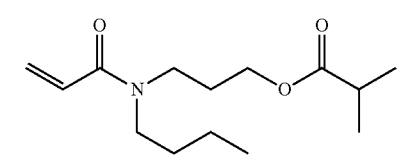
b4-5
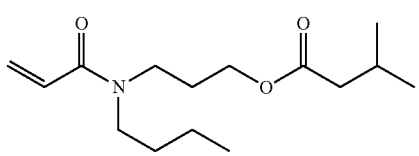
b4-6
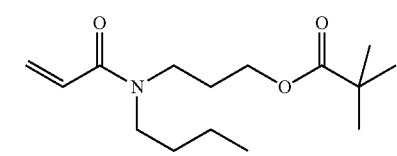
<<Group of Example Compounds b5>>
b5-1
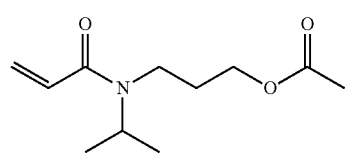
b5-2
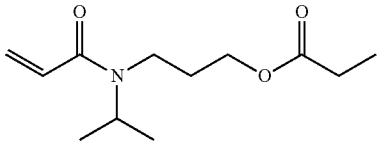

-continued
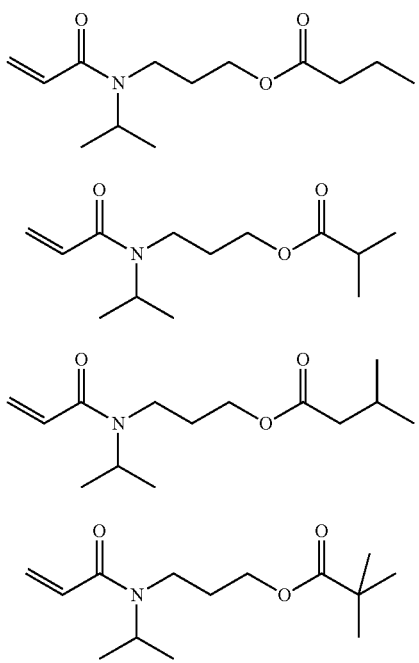
b5-3
b5-4
b5-5
b5-6
<<Group of Example Compounds b6>>
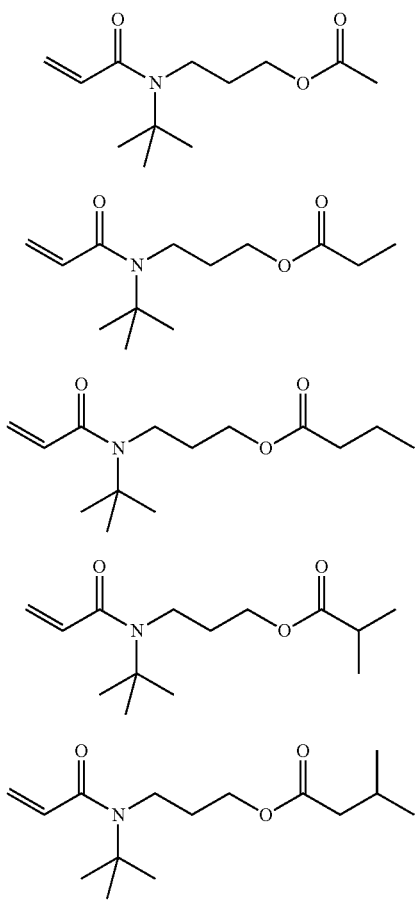
b6-1
b6-2
b6-3
b6-4
b6-5
-continued
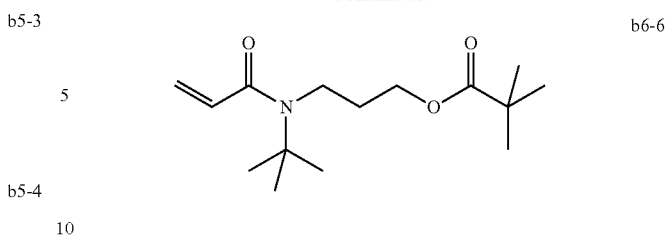
b6-6
The group of example compounds c includes groups of compounds c1 to c6 presented below. One of these compounds may be used alone or two or more of these compounds may be used in combination.
<<Group of Example Compounds c1>>
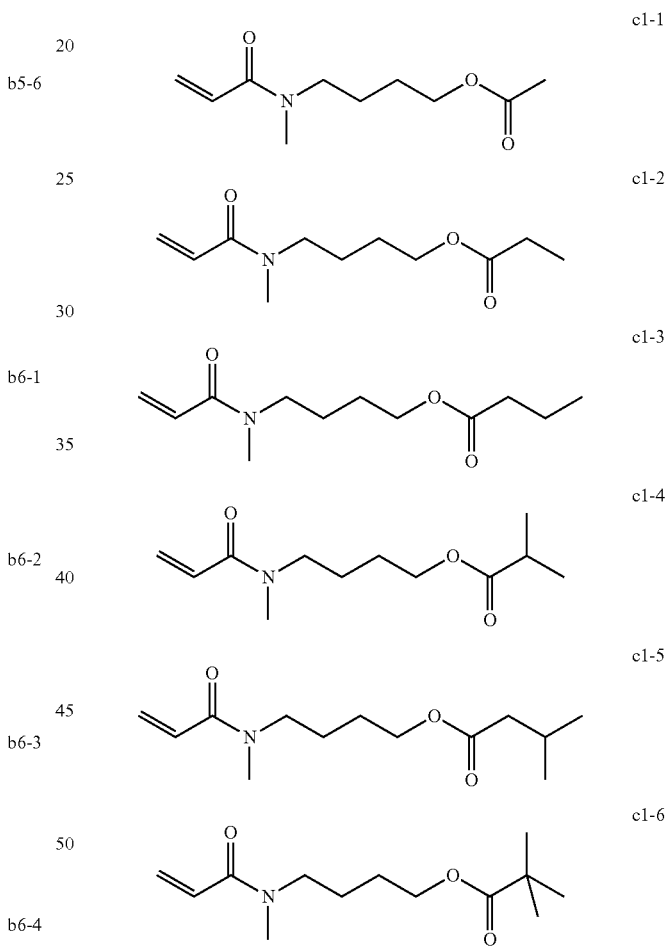
c1-1
c1-2
c1-3
c1-4
c1-5
c1-6
<<Group of Example Compounds c2>>
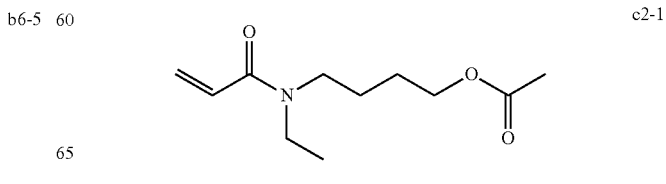
c2-1 c2-2
c2-3
c2-4
c2-5
c2-6
<<Group of Example Compounds c3>>
c3-1
c3-2
c3-3
c3-4
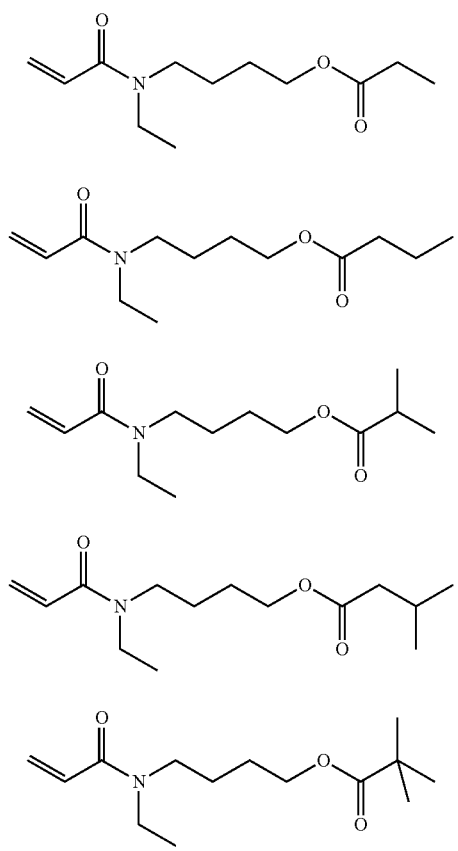
c3-5
c3-6
<<Group of Example Compounds c4>>
c4-1
c4-2
c4-3
c4-4
c4-5
c4-6
<<Group of Example Compounds c5>>
c5-1
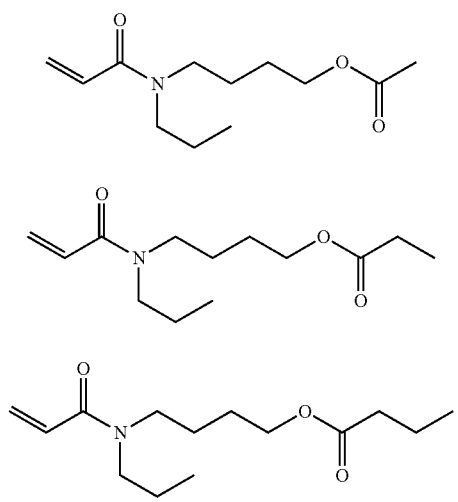
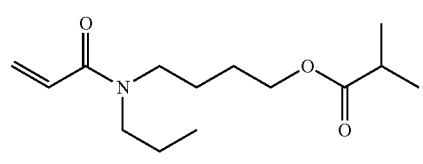

-continued
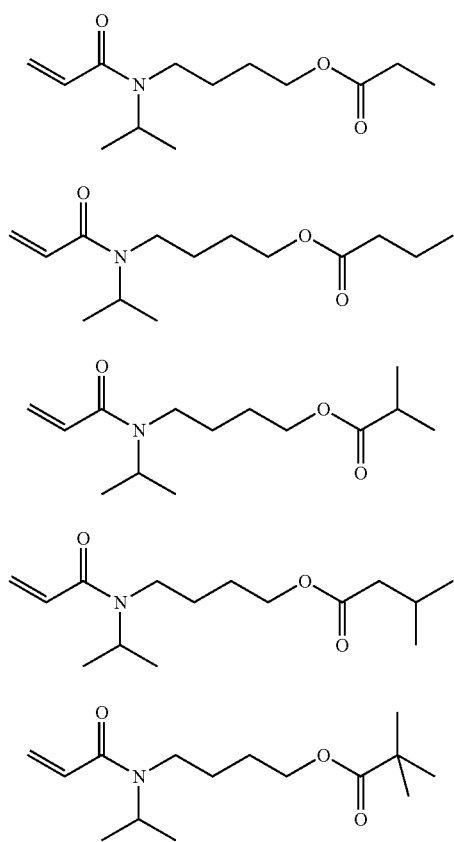
c5-2
c5-3
c5-4
c5-5
c5-6
<<Group of Example Compounds c6>>
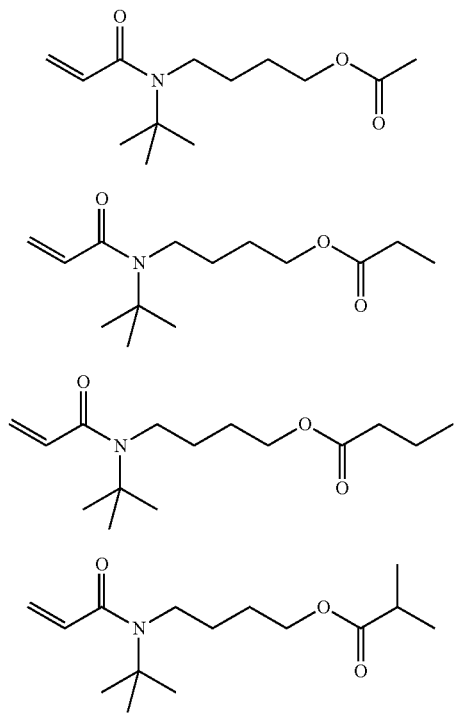
c6-1
c6-2
c6-3
c6-4
-continued
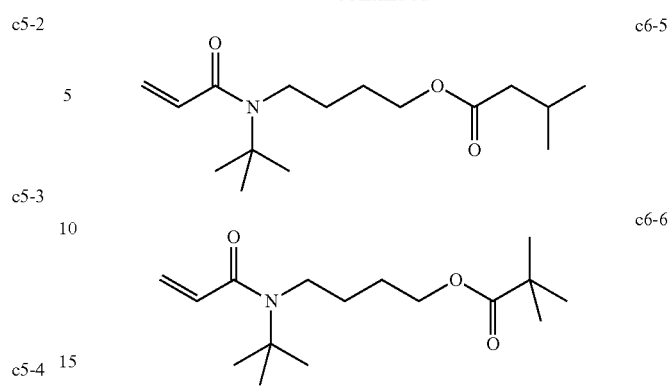
c6-5
c6-6
The group of example compounds d includes groups of compounds d1 to d6 presented below. One of these compounds may be used alone or two or more of these compounds may be used in combination.
<<Group of Example Compounds d1>>
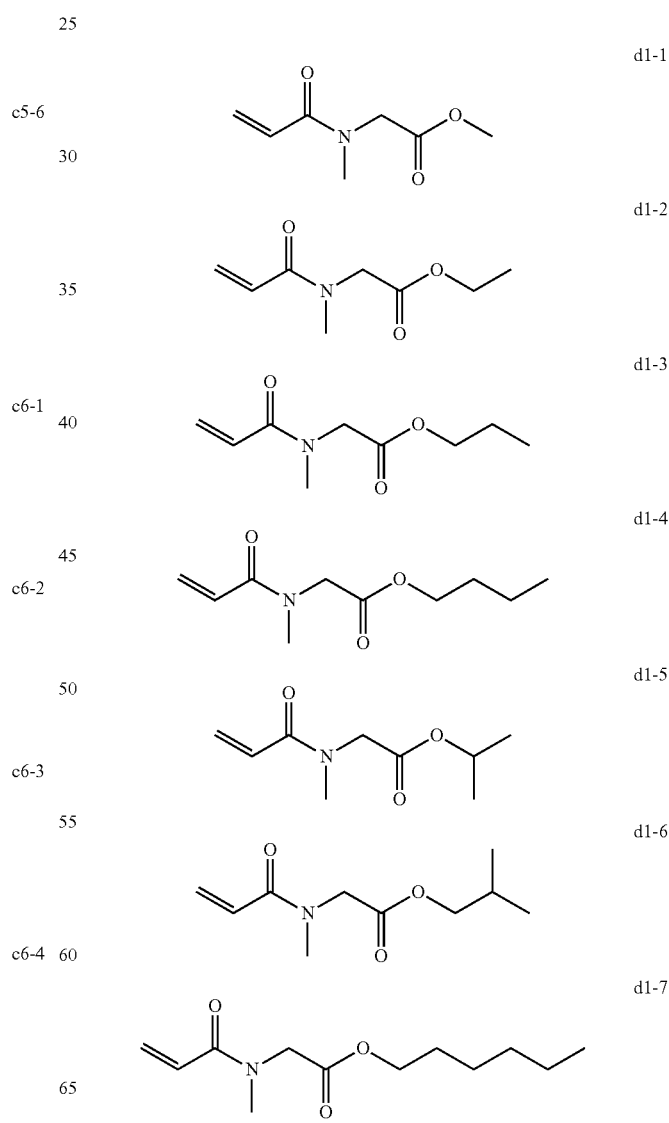
d1-1
d1-2
d1-3
d1-4
d1-5
d1-6
d1-7

-continued
d1-8
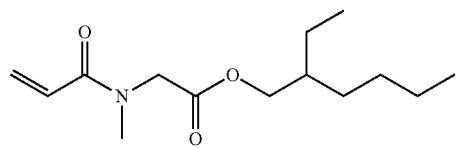
<<Group of Example Compounds d2>>
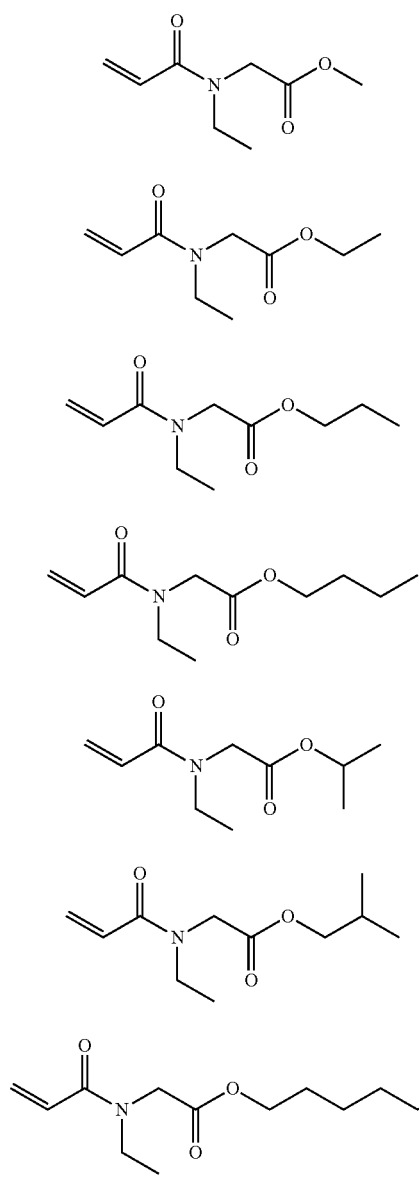
d2-1
d2-2
d2-3
d2-4
d2-5
d2-6
d2-7
d2-8
<<Group of Example Compounds d3>>
d3-1
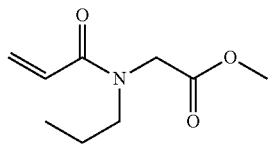
d3-2
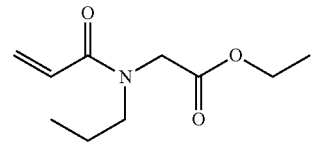
d3-3
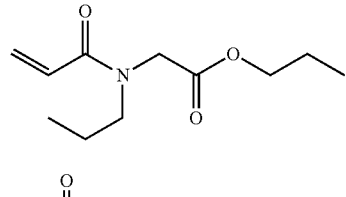
d3-4
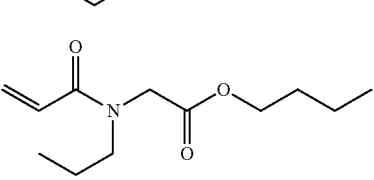
d3-5
d3-6
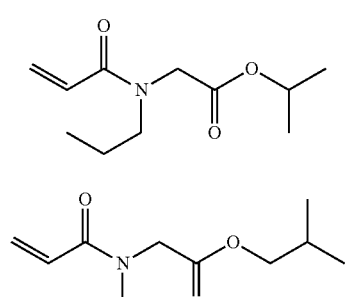
d3-7
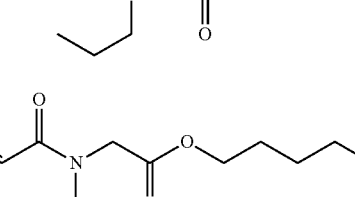
d3-8
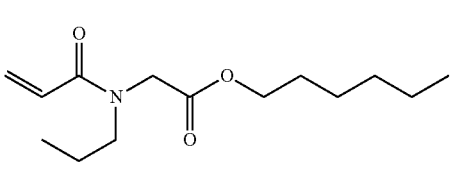
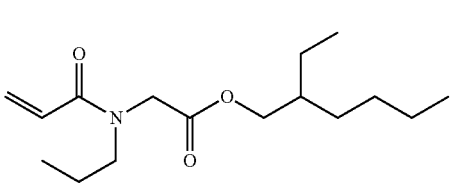
<<Group of Example Compounds d4>>
d4-1
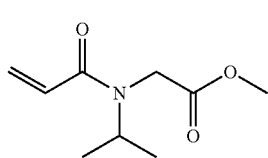

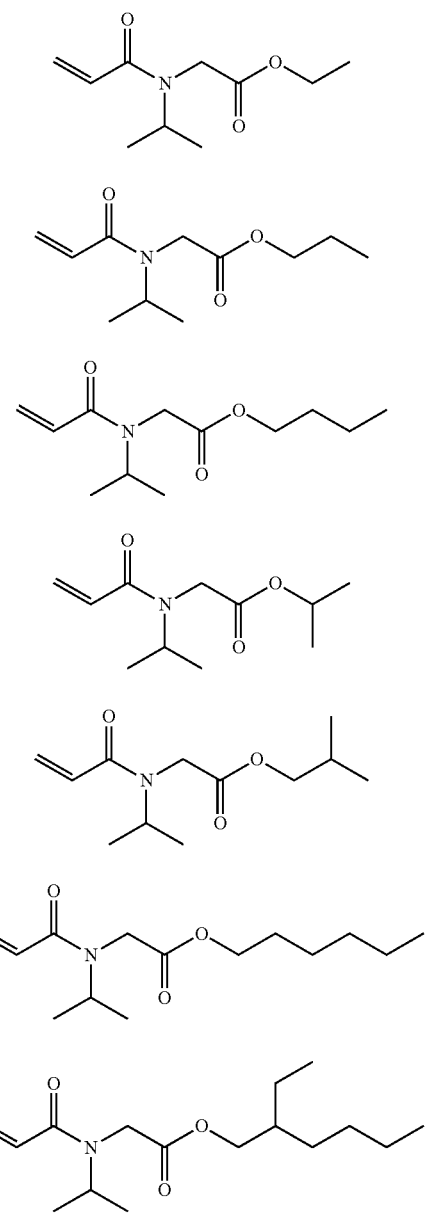
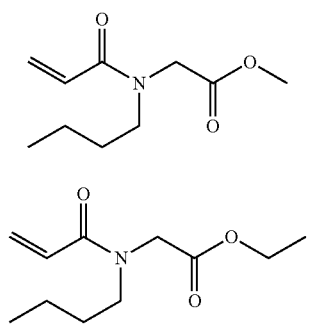
<<Group of Example Compounds d5>>
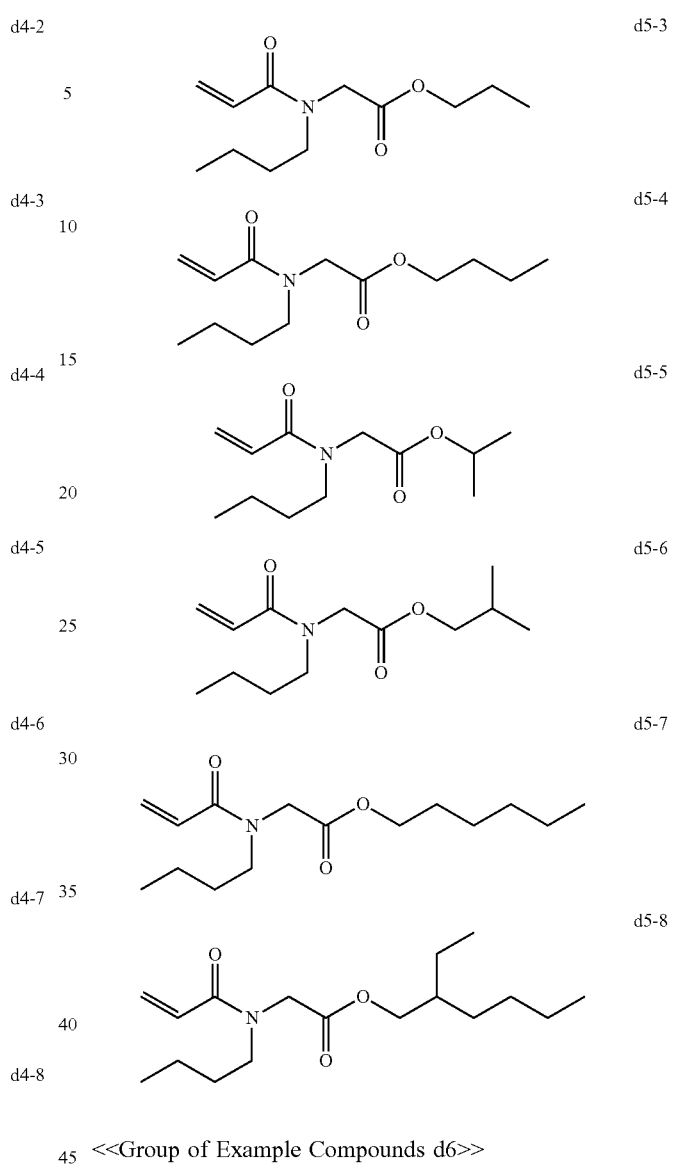
<<Group of Example Compounds d6>>
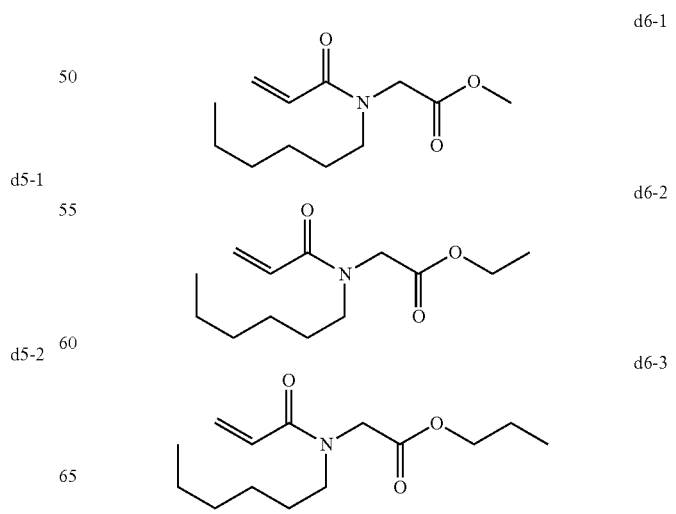

-continued
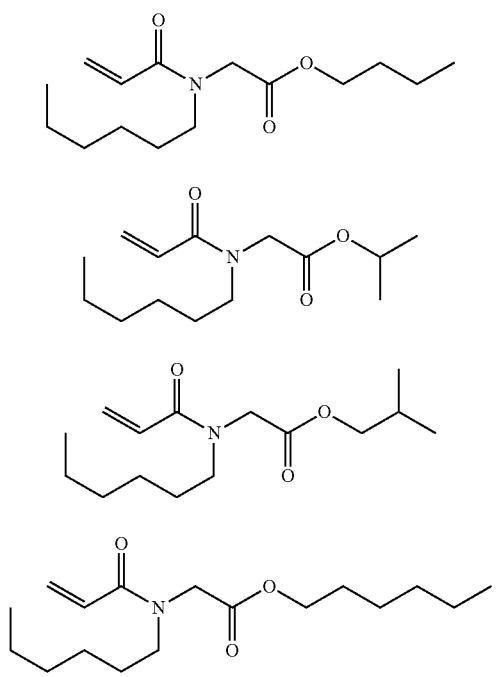
d6-4
d6-5
d6-6
d6-7
d6-8
The group of example compounds e includes groups of compounds e1 to e6 presented below. One of these compounds may be used alone or two or more of these compounds may be used in combination.
<<Group of Example Compounds e1>>
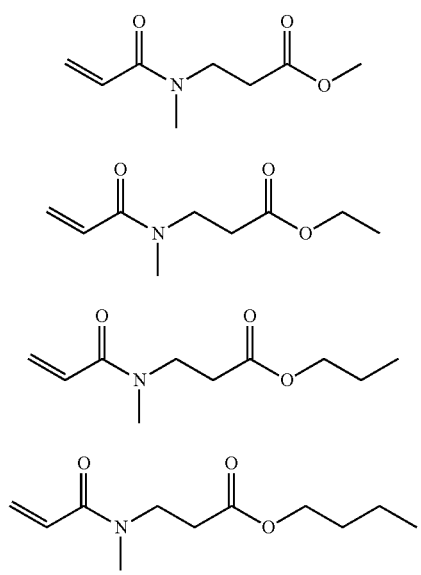
e1-1
e1-2
e1-3
e1-4
-continued
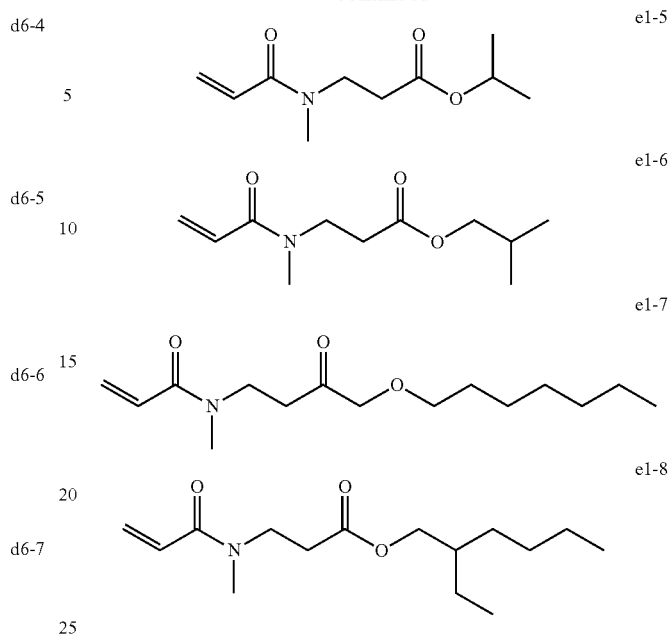
e1-5
e1-6
e1-7
e1-8
<<Group of Example Compounds e2>>
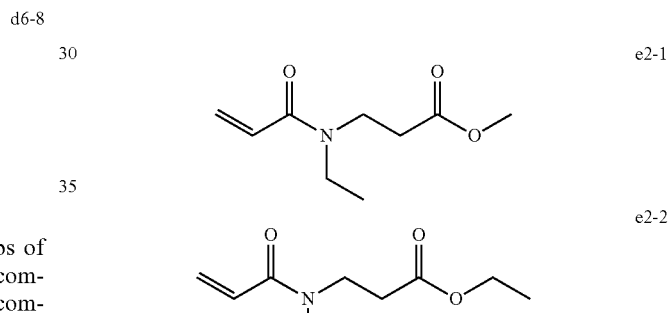
e2-1
e2-2
e2-3
e2-4
e2-5
e2-6 e2-7
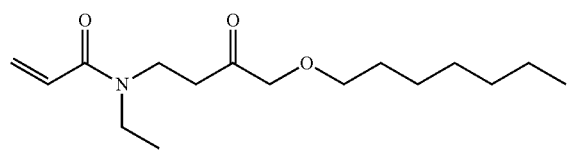
e2-8
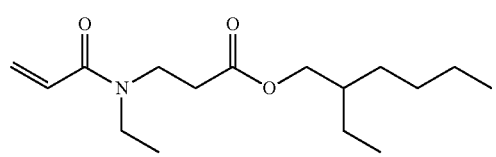
<<Group of Example Compounds e3>>
e3-1
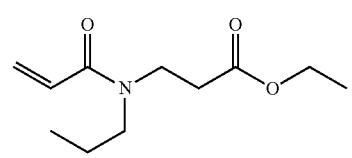
e3-2
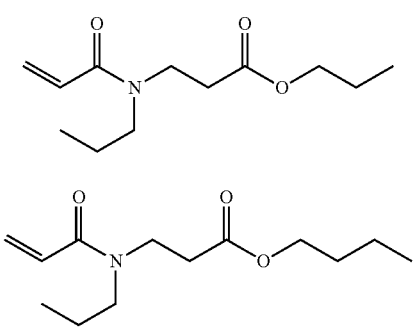
e3-3
e3-4
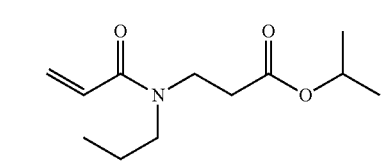
e3-5
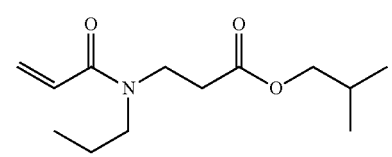
e3-6
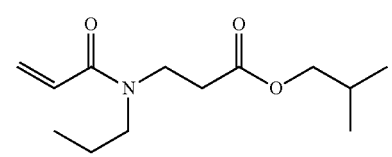
e3-7
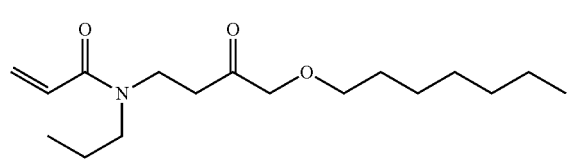
e3-8
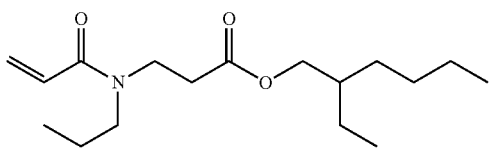
<<Group of Example Compounds e4>>
e4-1
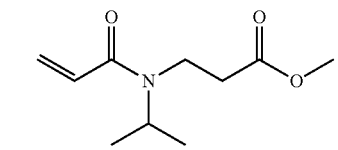
e4-2
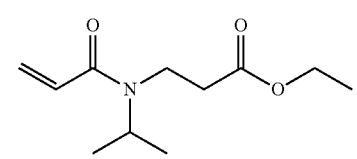
e4-3
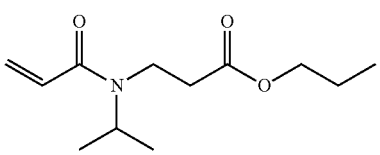
e4-4
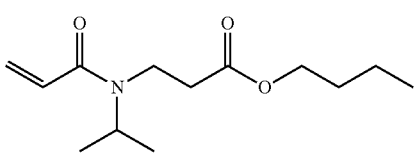
e4-5
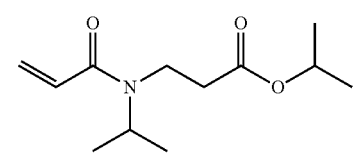
e4-6
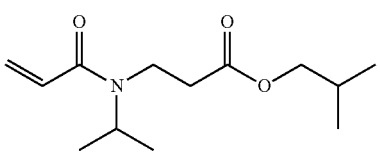
e4-7
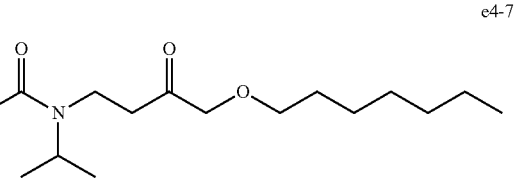
e4-8
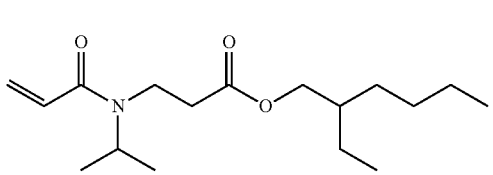

<<Group of Example Compounds e5>>
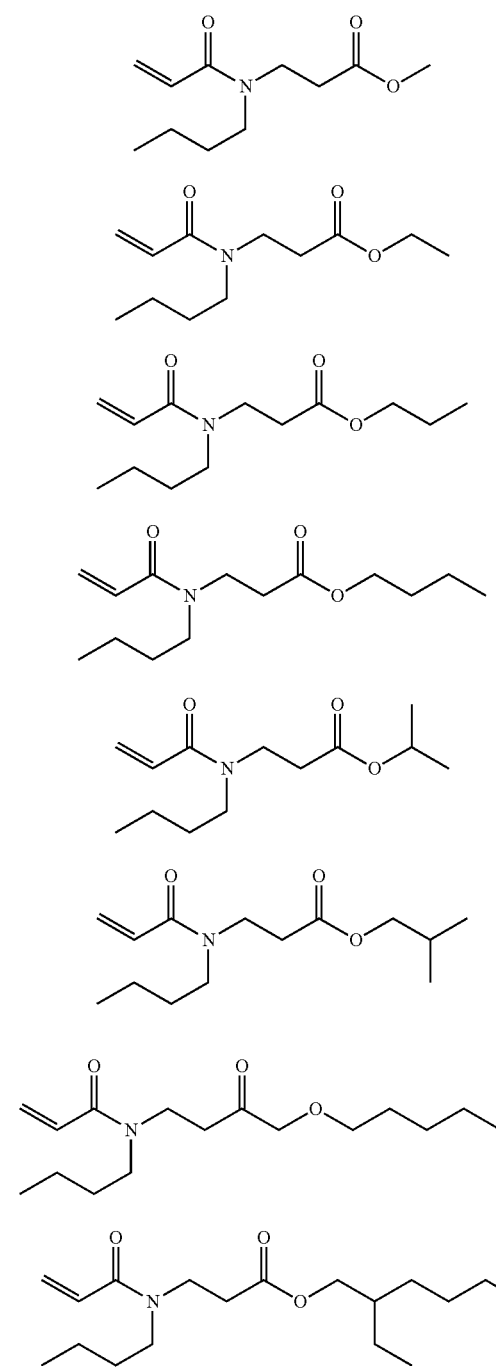
<<Group of Example Compounds e6>>
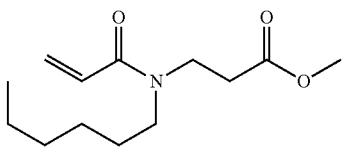
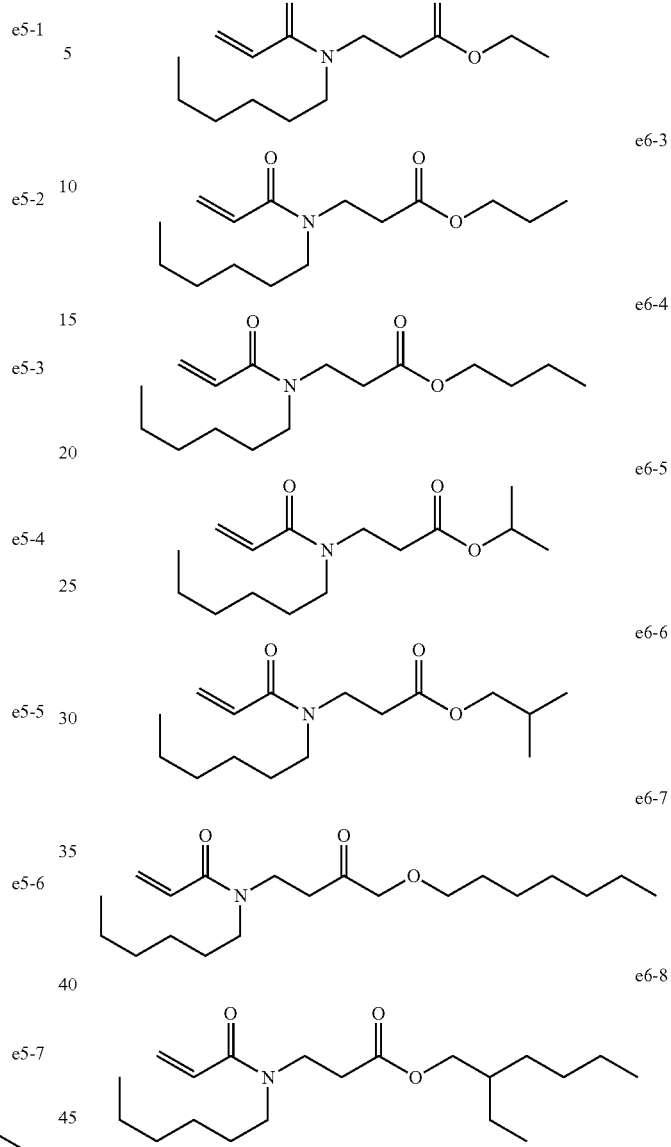
The group of example compounds f includes a group of compounds f1 presented below. One of these compounds may be used alone or two or more of these compounds may be used in combination.
<<Group of Example Compounds f1>>
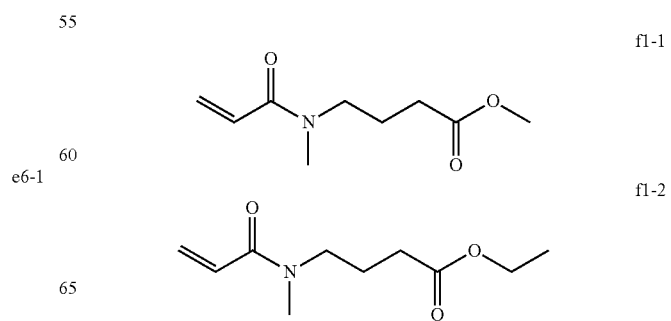

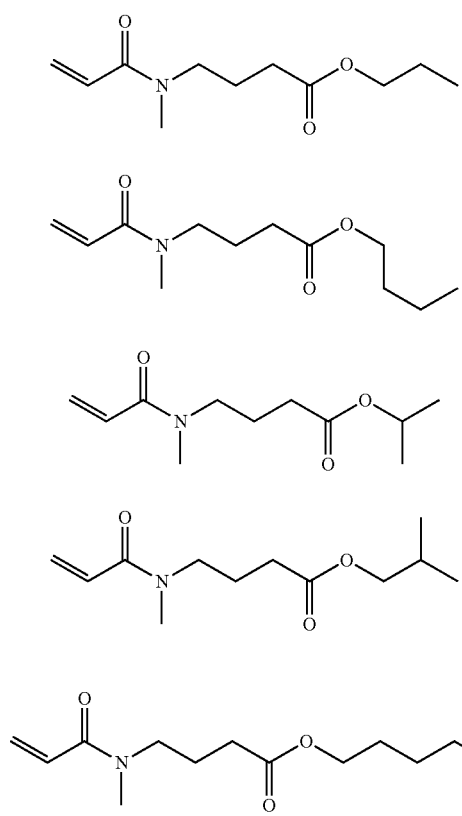
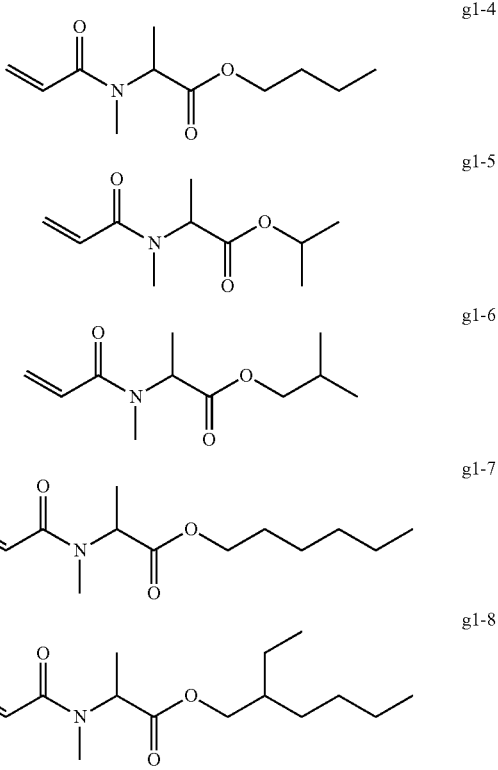
The group of example compounds g includes groups of compounds g1 to g6 presented below. One of these compounds may be used alone or two or more of these compounds may be used in combination.
<<Group of Example Compounds g1>>
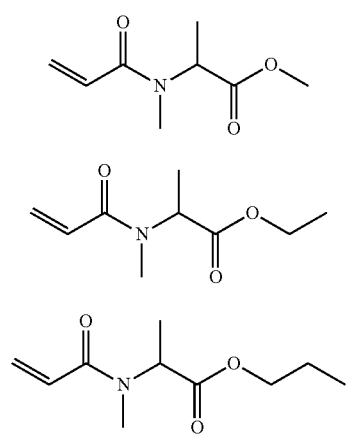
<<Group of Example Compounds g2>>
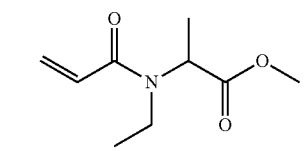
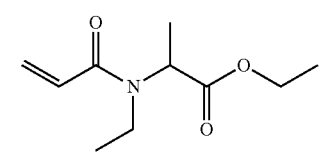
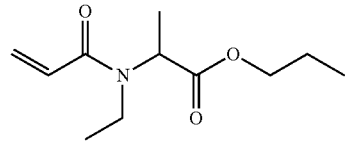
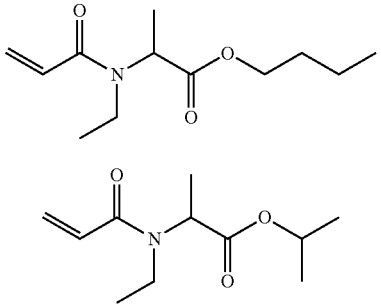

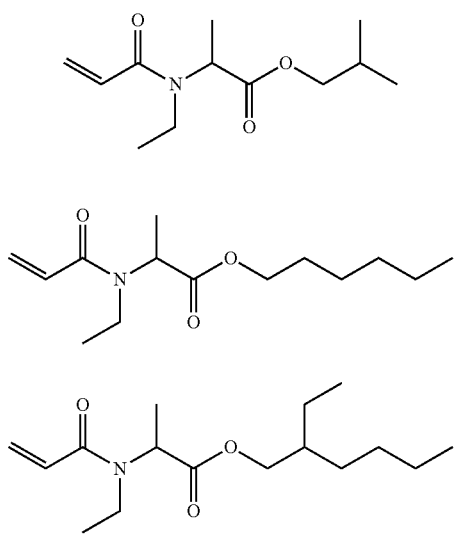
<<Group of Example Compounds g3>>
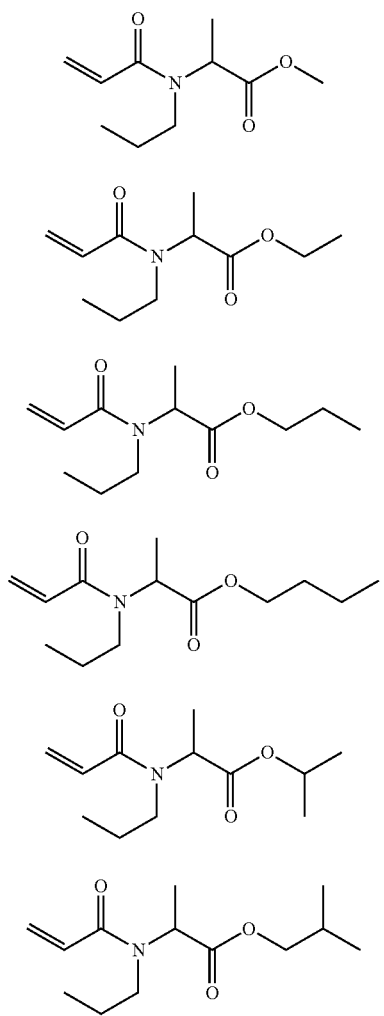
<<Group of Example Compounds g4>>

-continued
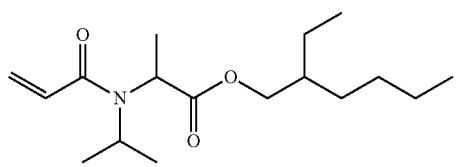
<<Group of Example Compounds g5>>
g5-1
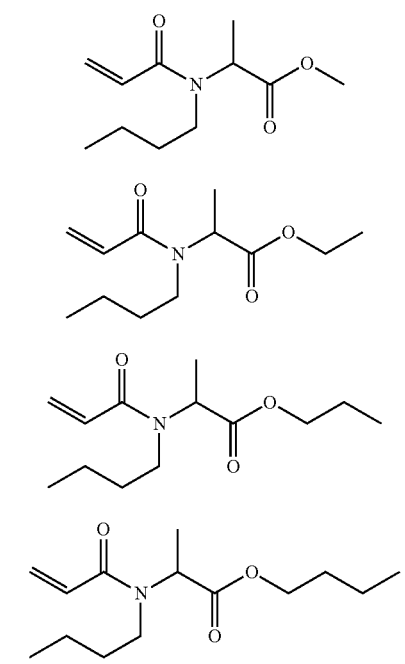
g5-2
g5-3
g5-4
g5-5
g5-6
g5-7
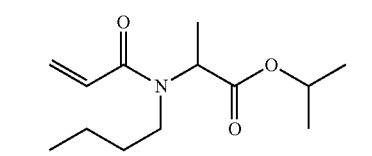
g5-8
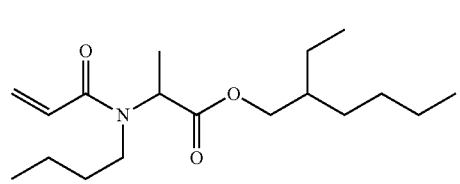
<<Group of Example Compounds g6>>
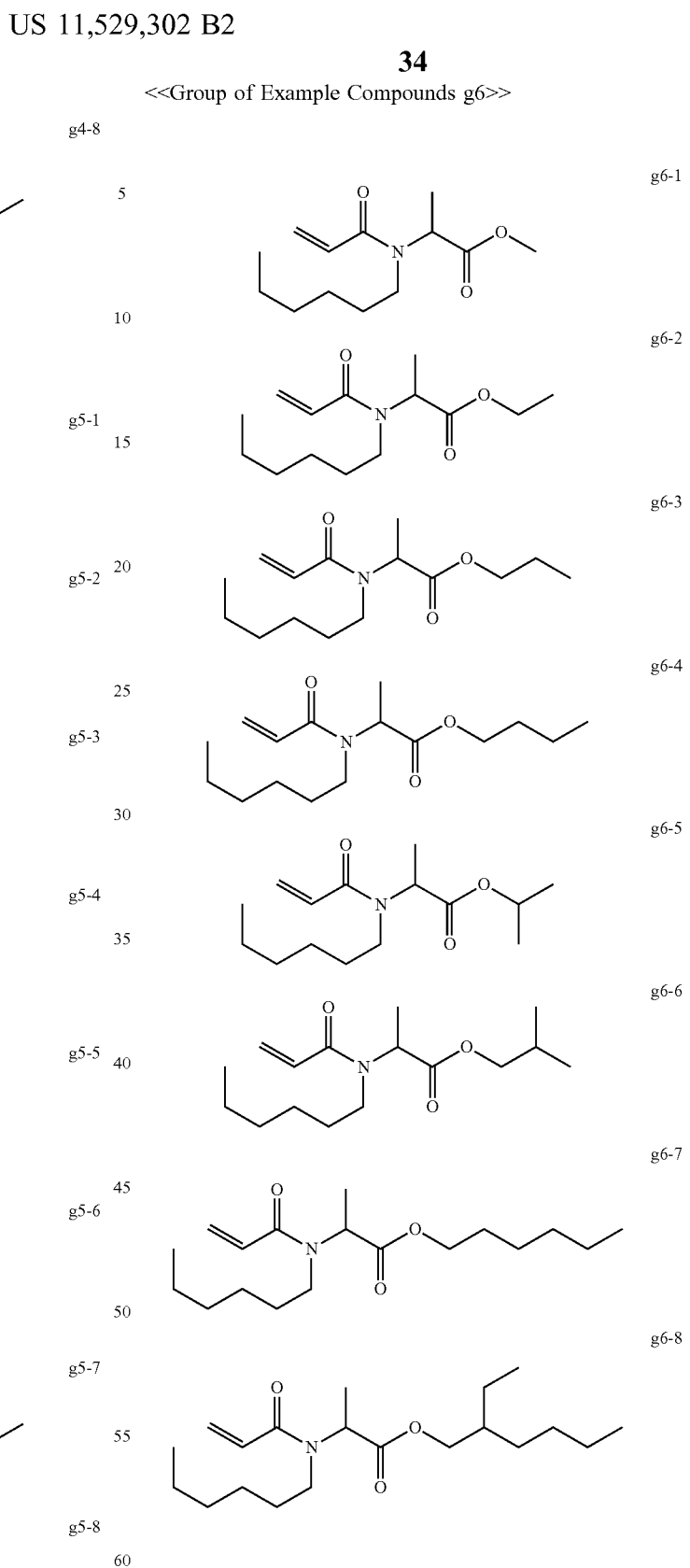
g6-1
g6-2
g6-3
g6-4
g6-5
g6-6
g6-7
g6-8
The group of example compounds h includes a group of compounds h1 presented below. One of these compounds may be used alone or two or more of these compounds may be used in combination.

<<Group of Example Compounds h1>>

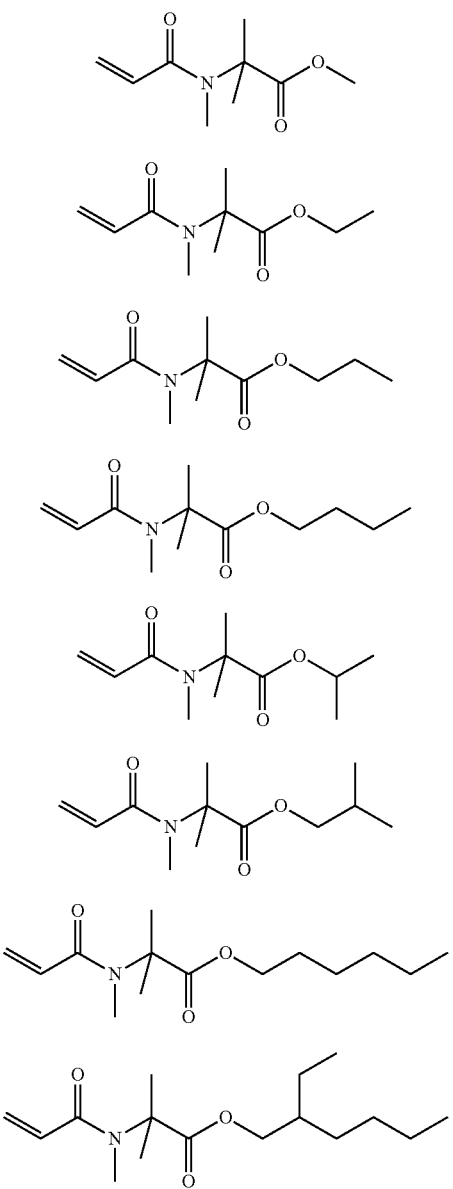

Among the groups of example compounds a to h, the example compound a1-1, the example compound a1-4, the example compound a6-1, the example compound d1-1, the example compound d1-2, the example compound d1-4, the example compound d1-5, the example compound d3-2, the example compound d4-1, the example compound d4-5, the example compound d6-1, the example compound d6-4, the example compound g1-1, the example compound g1-2, and the example compound g1-5 are preferable, and the example compound d1-1, the example compound d1-2, the example compound g1-1, the example compound g1-2, and the example compound g1-5 are more preferable in terms of curability.

As the acrylamide compound represented by general formula (1) above, two or more different compounds may be used as a mixture. In this case, examples of a different compound include a structural isomer. The mixing ratio is not particularly limited.

The content of the acrylamide compound is preferably 10% by mass or greater but 98% by mass or less, more preferably 30% by mass or greater but 90% by mass or less, and yet more preferably 30% by mass or greater but 70% by mass or less relative to the total amount of the composition.

<Urethane (meth)acrylate>

As the urethane (meth)acrylate having a SI value of 3 or less in a skin sensitization test, a commercially available product can be used. Examples of the commercially available product include CN9002 available from Tomoe Engineering Co., Ltd.

The urethane (meth)acrylate has a SI value of 3 or less. Use of the urethane (meth)acrylate having a SI value of 3 or less ensures safety in terms of skin sensitizing potential.

The SI (Stimulation Index) value is an indicator of the degree of skin sensitizing potential, and measured by LLNA method stipulated by, for example, OECD test guideline 429.

It is judged that a substance has no sensitizing potential when the SI value is 3 or less. This is disclosed in the following document (referential document: the September 2005 issue of "Functional Materials", Vol. 25, No. 9, P55).

A smaller SI value indicates a lower degree of skin sensitizing potential. The SI value is more preferably 2 or less and yet more preferably 1.6 or less.

The content of the urethane (meth)acrylate having a SI value of 3 or less in a skin sensitization test is preferably 1% by mass or greater but 50% by mass or less, more preferably 5% by mass or greater but 40% by mass or less, and yet more preferably 10% by mass or greater but 40% by mass or less relative to the total amount of the composition.

When the content of the urethane (meth)acrylate is 1% by mass or greater but 50% by mass or less, odor reduction can be achieved and a cured product safe in terms of skin sensitizing potential can be obtained.

<Other Polymerizable Compounds than Acrylamide Compound Represented by General Formula (1) and Urethane (Meth)Acrylate Having SI Value of 3 or Less>

As other polymerizable compounds than the acrylamide compound represented by general formula (1) and the urethane meth(acrylate having a SI value of 3 or less, known polymerizable monomers, of which representative examples are (meth)acrylic acid esters, can be used.

Combined use of other polymerizable compounds makes it easy to adjust, for example, the curability and viscosity of the composition and the hardness and close adhesiveness of a cured product depending on the purpose of use.

Examples of the (meth)acrylic acid esters include methyl (meth)acrylate, ethyl (meth)acrylate, n-butyl (meth)acrylate, allyl(meth)acrylate, glycidyl (meth)acrylate, 2-(dimethylamino)ethyl (meth)acrylate, 2-hydroxyethyl (meth)acrylate, 2-butoxyethyl (meth)acrylate, ethyl carbitol (meth)acrylate, cyclohexyl (meth)acrylate, tetrahydrofurfuryl (meth)acrylate, 2-(2-vinyloxyethoxy)ethyl (meth)acrylate, benzyl (meth)acrylate, 2-phenoxyethyl (meth)acrylate, 2-hydroxy-3-phenoxypropyl (meth)acrylate, isobornyl (meth)acrylate, ethylene glycol di(meth)acrylate, diethylene glycol di(meth)acrylate, triethylene glycol di(meth)acrylate, tetraethylene glycol di(meth)acrylate, polyethylene glycol di(meth)acrylate, propylene glycol di(meth)acrylate, dipropylene glycol di(meth)acrylate, tripropylene glycol di(meth)acrylate, tetrapropylene glycol di(meth)acrylate, polypropylene glycol di(meth)acrylate, neopentyl glycol di(meth)acrylate, ethoxylated neopentyl glycol di(meth)acrylate, propoxylated neopentyl glycol di(meth)acrylate, 1,6-hexanediol di(meth)acrylate, 1,9-nonanediol di(meth)acrylate, pentaerythritol tri(meth)acrylate, pentaerythritol tetra(meth)

acrylate, dipentaerythritol hexa(meth)acrylate, and trimethylolpropane tri(meth)acrylate.

Examples of other polymerizable compounds than the acrylamide compound represented by general formula (1) include (meth)acryloyl morpholine.

The content of the other polymerizable compounds than the acrylamide compound represented by general formula (1) is preferably 1% by mass or greater but 60% by mass or less and more preferably 5% by mass or greater but 40% by mass or less relative to the total amount of the composition.

<Polymerization Initiator Having Molecular Weight of 800 or Greater>

The polymerization initiator having a molecular weight of 800 or greater is not particularly limited and may be appropriately selected depending on the intended purpose. Examples of the polymerization initiator having a molecular weight of 800 or greater include polyethylene glycol 200-di(β-4(4-(2-dimethylamino-2-benzyl)butanonylphenyl) piperazine) (available from IGM, "OMNIPOL 910"), 1,3-di({α-[1-chloro-9-oxo-9H-thioxanthen-4-yl)oxy]acetyl poly[oxy(1-methylethylene)]}oxy)-2,2-bis({α-[1-chloro-9-oxo-9H-thioxanthe n-4-yl)oxy]acetyl poly[oxy(1-methylethylene)]}oxymethyl)propane (available from Lambson Limited, "SPEEDCURE 7010"), a mixture of 1,3-di({α-4-(dimethylamino)benzoyl poly[oxy(1-methylethylene)] }oxy)-2,2-bis({(α-4-(dimethylamino)benzoyl poly[oxy(1-methylethylene)]}oxymethyl)propane with {α-4-(dimethylamino)benzoyl poly(oxyethylene)-poly[oxy(1-methylethylene)]-poly(oxyethylene)}4-(dimethylamino) benzoate (available from Lambson Limited, "SPEEDCURE 7040"), polybutylene glycol bis(9-oxo-9H-thioxanthinyloxy) acetate (available from IGM, "OMNIPOL TX"), a polymeric thioxanthene compound (available from Rahn AG, "GENOPOL TX-2"), and oligomers of 2-hydroxy-1-(4-isopropenylphenyl)-2-methylpropan-1-one [benzene, (1-methylethynyl)-, homopolymers, and ar-(2-hydroxy-2-methyl-1-oxopropyl) derivatives](available from IGM, "ESACURE ONE"). One of these polymerization initiators may be used alone or two or more of these polymerization initiators may be used in combination.

The polymerization initiator may be referred to simply as initiator.

The polymerization initiator having a molecular weight of 800 or greater is an α-aminoketone-based polymerization initiator, and has an absorption sensitivity to the wavelengths of ultraviolet light-emitting diodes having emission peak wavelengths of 365 nm, 385 nm, 395 nm, or 405 nm. As the polymerization initiator having an absorption sensitivity to these emission peak wavelengths, acylphosphine oxide-based polymerization initiators and α-aminoketone-based polymerization initiators are known. However, for example, "bis(2,4,6-trimethylbenzoyl)-phenyl phosphine oxide, product name: IRGACURE 819", which is known as an acylphosphine oxide-based polymerization initiator, has a poor solubility in the acrylamide compound having an ester structure used in the composition of the present disclosure. Hence, it has been difficult to realize a practical level of curability by irradiation of an active-energy-ray-curable composition containing a polymerization initiator having such a poor solubility as described above with ultraviolet rays having an emission peak in the wavelength range of from 365 nm through 405 nm, using an ultraviolet light-emitting diode.

On the other hand, the polymerization initiator having a molecular weight of 800 or greater has an excellent solubility in the acrylamide compound having an ester structure used in the composition of the present disclosure. Hence, it is possible to realize a practical level of curability by irradiation of an active-energy-ray-curable composition containing the acrylamide compound represented by general formula (1) and having an ester structure and the polymerization initiator having a molecular weight of 800 or greater with ultraviolet rays having an emission peak in the wavelength range of 365 nm or greater but 405 nm or less, using an ultraviolet light-emitting diode.

The content of the polymerization initiator having a molecular weight of 800 or greater is preferably 1% by mass or greater but 20% by mass or less, more preferably 3% by mass or greater but 15% by mass or less, and yet more preferably 5% by mass or greater but 10% by mass or less relative to the total amount of the composition.

The mass ratio of the content of the acrylamide compound represented by general formula (1) above to the content of the polymerization initiator having a molecular weight of 800 or greater in the composition is preferably 5 or greater but 25 or less, more preferably 8 or greater but 20 or less, and yet more preferably 9 or greater but 19 or less.

<Other Polymerization Initiators than Polymerization Initiator Having Molecular Weight of 800 or Greater>

As other polymerization initiators than the polymerization initiator having a molecular weight of 800 or greater, there are a thermal polymerization initiator and a photopolymerization initiator.

The photopolymerization initiator may be any substance that can produce active species such as radicals and cations in response to the energy of active energy rays and initiate polymerization of a polymerizable compound (e.g., a monomer and an oligomer). As such a photopolymerization initiator, one, or two or more in combination, selected from, for example, known radical polymerization initiators, cationic polymerization initiators, and base generators may be used. Above all, radical polymerization initiators are preferable.

Examples of radical polymerization initiators include aromatic ketones, acylphosphine oxide compounds, aromatic onium salt compounds, organic peroxides, thio compounds (e.g., thioxanthone compounds and thiophenyl group-containing compounds), hexaaryl biimidazole compounds, ketoxime ester compounds, borate compounds, adinium compounds, metallocene compounds, active ester compounds, carbon-halogen bond-containing compounds, and alkylamine compounds.

The content of other polymerization initiators than the polymerization initiator having a molecular weight of 800 or greater is preferably 0.1% by mass or greater but 10% by mass or less and more preferably 0.5% by mass or greater but 5% by mass or less relative to the total amount of the composition.

Combined use of other polymerization initiators than the polymerization initiator having a molecular weight of 800 or greater makes it easy to adjust, for example, the curability and viscosity of the composition and the hardness and close adhesiveness of a cured product depending on the purpose of use.

The composition of the present disclosure may further contain a sensitizer in order to promote decomposition of the polymerization initiator by active energy ray irradiation.

The sensitizer absorbs active energy rays to become an electroexcited state and contacts the polymerization initiator while in that state, to promote a chemical change (decomposition, or production of radicals, acids, or bases) of the polymerization initiator by the action of, for example, electron transfer, energy transfer, and heat generation. The mass ratio of the sensitizer relative to the photopolymerization initiator is preferably $5 \times 10^{-3}$ or greater but 200 or less, and more preferably 0.02 or greater but 50 or less.

The sensitizer is not particularly limited and may be appropriately selected depending on the intended purpose. A sensitizing pigment having an absorption wavelength in a wavelength range of 350 nm or greater but 450 nm or less can be used. Examples of the sensitizer include polynuclear aromatic series (e.g., pyrene, perylene, and triphenylene), xanthenes (e.g., fluorescein, eosin, erythrosine, rhodamine B, and rose Bengal), cyanines (e.g., thiacarbocyanine and oxacarbocyanine), merocyanines (e.g., merocyanine and carbomerocyanine), thiazines (e.g., thionine, methylene blue, and toluidine blue), acridines (e.g., acridine orange, chloro flavin, and acriflavine), anthraquinones (e.g., anthraquinone), squaryliums (e.g., squarylium), and coumarins (e.g., 7-diethyl amino-4-methyl coumarin).

The composition of the present disclosure may further contain a co-sensitizer. The co-sensitizer further improves sensitivity of a sensitizing pigment to active energy rays or suppresses inhibition of polymerization of the polymerizable compound by oxygen.

The co-sensitizer is not particularly limited and may be appropriately selected depending on the intended purpose. Examples of the co-sensitizer include: amine-based compounds such as triethanolamine, p-dimethyl aminobenzoic acid ethyl ester, p-formyl dimethyl aniline, and p-methyl thiodimethyl aniline; thiols such as 2-mercapto benzothiazole, 2-mercapto benzoxazole, 2-mercapto benzoimidazole, 2-mercapto-4(3H)-quinazoline, and 3-mercapto naphthalene; and sulfides.

The composition of the present disclosure may further contain a polymerization inhibitor. This can increase the storage property (storage stability) of the composition. This also makes it possible to prevent clogging of a head due to thermal polymerization, in the case of discharging the composition by heating the composition and decreasing the viscosity of the composition.

The polymerization inhibitor is not particularly limited and may be appropriately selected depending on the intended purpose. Examples of the polymerization inhibitor include hydroquinone, benzoquinone, p-methoxyphenol, TEMPO, TEMPOL, and aluminum-cupferron complex. The content of the polymerization inhibitor is preferably 200 ppm or greater but 20,000 ppm or less relative to the total amount of the composition.

<Other Components>

Examples of other components that may be contained in the composition of the present disclosure as needed include a colorant, an organic solvent, a stabilizer, a plasticizer, a thickener, an antiseptic, a heat dissipating agent, a biocompatible substance, and a fiber reinforcing material.

As the colorant, various pigments and dyes may be used that impart black, white, magenta, cyan, yellow, green, orange, and gloss colors such as gold and silver, depending on the intended purpose of the composition of the present disclosure and requisite properties thereof.

A content of the colorant in the composition is not particularly limited, and may be appropriately determined considering, for example, a desired color density and dispersibility of the colorant in the composition. However, it is preferably from 0.1% by mass to 20% by mass relative to the total mass of the composition. Incidentally, the composition of the present disclosure does not necessarily contain a colorant but can be clear and colorless. In such a case, for example, such a clear and colorless composition is good for an overcoating layer to protect an image.

The pigment can be either inorganic or organic, and two or more of the pigments can be used in combination.

Specific examples of the inorganic pigments include, but are not limited to, carbon blacks (C.I. Pigment Black 7) such as furnace black, lamp black, acetylene black, and channel black, iron oxides, and titanium oxides.

Specific examples of the organic pigments include, but are not limited to, azo pigments such as insoluble azo pigments, condensed azo pigments, azo lakes, and chelate azo pigments, polycyclic pigments such as phthalocyanine pigments, perylene pigments, perinone pigments, anthraquinone pigments, quinacridone pigments, dioxane pigments, thioindigo pigments, isoindolinone pigments, and quinofuranone pigments, dye chelates (e.g., basic dye chelates, acid dye chelates), dye lakes (e.g., basic dye lakes, acid dye lakes), nitro pigments, nitroso pigments, aniline black, and daylight fluorescent pigments.

In addition, a dispersant is optionally added to enhance the dispersibility of pigment. The dispersant has no particular limit and can be, for example, polymer dispersants conventionally used to prepare pigment dispersion (material).

The dyes include, for example, acidic dyes, direct dyes, reactive dyes, basic dyes, and combinations thereof.

<Organic Solvent>

The composition of the present disclosure optionally contains an organic solvent although it is preferable to spare it. The composition free of an organic solvent, in particular volatile organic compound (VOC), is preferable because it enhances safety at where the composition is handled and makes it possible to prevent pollution of the environment. Incidentally, the organic solvent represents a conventional non-reactive organic solvent, for example, ether, ketone, xylene, ethyl acetate, cyclohexanone, and toluene, which is clearly distinguished from reactive monomers. Furthermore, "free of" an organic solvent means that no organic solvent is substantially contained. The content thereof is preferably less than 0.1 percent by mass.

The plasticizer can impart flexibility to a polymer formed of a monomer. Examples of the plasticizer include polyethylene glycol ester, terminally capped polyester, butyl stearate, lauric acid, dioctyl glutarate, triglyceride, dioctyl oxalate, triethyl phosphate, and acetyl tributyl citrate.

Examples of the thickener include polycyano acrylate, polylactic acid, polyglycolic acid, polycaprolactone, polyacrylic acid alkyl ester, and polymethacrylic acid alkyl ester.

Examples of the antiseptic include hitherto used substances that do not cause a monomer to initiate polymerization, such as potassium sorbate, sodium benzoate, sorbic acid, and chlorocresol.

The fiber reinforcing material is not particularly limited. Examples of the fiber reinforcing material include natural rubbers or synthetic rubbers such as styrene and acrylonitrile for reinforcing shock resistance of the composition.

The stabilizer performs the function of suppressing polymerization of a monomer during storage. Examples of the stabilizer include anionic stabilizer and free radical stabilizers. Examples of the former include metaphosphoric acid, maleic acid, maleic anhydride, alkyl sulfonic acid, phosphorus pentoxide, iron (III) chloride, antimony oxide, 2,4,6-trinitrophenol, thiol, alkyl sulfonyl, alkyl sulfone, alkyl sulfoxide, alkyl sulfite, sultone, sulfur dioxide, and sulfur trioxide. Examples of the latter include hydroquinone, catechol, and derivatives of these substances.

<Preparation of Composition>

The composition of the present disclosure can be prepared by using the components described above. The preparation devices and conditions are not particularly limited. For example, the composition can be prepared by subjecting the acrylamide compound represented by general formula (1) above, the urethane (meth)acrylate having a SI value of 3.0 or less, the polymerization initiator having a molecular weight of 800 or greater, a pigment, a dispersant, etc., to a dispersion treatment using a dispersing machine such as a ball mill, a kitty mill, a disk mill, a pin mill, and a DYNO-MILL to prepare a pigment liquid dispersion, and further mixing the pigment liquid dispersion with a polymerization inhibitor and a surfactant.

<Viscosity>

The viscosity of the composition of the present disclosure has no particular limit because it can be adjusted depending on the purpose and application devices. For example, if an ejecting device that ejects the composition from nozzles is employed, the viscosity thereof is preferably in the range of 3 mPa·s to 40 mPa·s, more preferably 5 mPa·s to 15 mPa·s, and particularly preferably 6 mPa·s to 12 mPa·s in the temperature range of 20 degrees C. to 65 degrees C., preferably at 25 degrees C. In addition, it is particularly preferable to satisfy this viscosity range by the composition free of the organic solvent described above. Incidentally, the viscosity can be measured by a cone plate rotary viscometer (VISCOMETER TVE-22L, manufactured by TOKI SANGYO CO., LTD.) using a cone rotor (1° 34'×R24) at a number of rotation of 50 rpm with a setting of the temperature of hemathermal circulating water in the range of 20 degrees C. to 65 degrees C. VISCOMATE VM-150III can be used for the temperature adjustment of the circulating water.

<Curing Unit>

Examples of a curing unit configured to cure the composition of the present disclosure include thermal curing or curing by active energy rays. Of these units, curing by active energy rays is preferable.

Active energy rays used for curing the composition of the present disclosure are not particularly limited, so long as they are able to give necessary energy for allowing polymerization reaction of polymerizable components in the composition to proceed. Examples of the active energy rays include electron beams, α-rays, ß-rays, γ-rays, and X-rays, in addition to ultraviolet rays. When a light source having a particularly high energy is used, polymerization reaction can be allowed to proceed without a polymerization initiator. In addition, in the case of irradiation with ultraviolet ray, mercury-free is preferred in terms of protection of environment. Therefore, replacement with GaN-based semiconductor ultraviolet light-emitting devices is preferred from industrial and environmental point of view. Furthermore, ultraviolet light-emitting diode (UV-LED) and ultraviolet laser diode (UV-LD) are preferable as an ultraviolet light source. Small sizes, long time working life, high efficiency, and high cost performance make such irradiation sources desirable.

Above all, in terms of energy saving and device downsizing, ultraviolet rays emitted by an ultraviolet light-emitting diode (hereinafter, may also be referred to as UV-LED) and having a peak in a wavelength range of 285 nm or greater but 405 nm or less (preferably, 365 nm or greater but 405 nm or less) are preferable. Generally, the light absorption spectrum of polymerization initiators is broad, and use of UV-LED configured to emit a narrow specific wavelength range makes it difficult to improve the curability of compositions. Hence, use of the composition of the present disclosure excellent in curability even if UV-LED is used is preferable.

<Application Field>

The application field of the composition of the present disclosure is not particularly limited. It can be applied to any field where active-energy-ray-curable compositions are used. For example, the composition is selected to a particular application and used for a resin for processing, a paint, an adhesive, an insulant, a releasing agent, a coating material, a sealing material, various resists, and various optical materials.

Furthermore, the composition of the present disclosure can be used to form two-dimensional texts, images, and designed coating film on various substrates and in addition used as a solid object forming material to form a three-dimensional object. This three dimensional object forming material may also be used as a binder for powder particles used in a powder layer laminating method of forming a three-dimensional object by repeating curing and layer-forming of powder layers, and as a three-dimensional object constituent material (a model material) and a supporting member used in an additive manufacturing method (a stereolithography method) as illustrated in FIG. 1 and FIGS. 2A to 2D. FIG. 1 is a diagram illustrating a method of additive manufacturing (to be described in detail below) to sequentially form layers of the composition of the present disclosure one on top of the other by repeating discharging the composition to particular areas followed by curing upon irradiation of an active energy ray. FIGS. 2A to 2D are each a diagram illustrating a method of additive manufacturing to sequentially form cured layers 6 having respective predetermined forms one on top of the other on a movable stage 3 by irradiating a storing pool (storing part) 1 of the composition 5 of the present disclosure with the active energy ray 4.

An apparatus for fabricating a three-dimensional object by the composition of the present disclosure is not particularly limited and can be a known apparatus. For example, the apparatus includes a containing device, a supplying device, and a discharging device of the composition, and an active energy ray irradiator.

In addition, the present disclosure includes cured materials obtained by curing the composition and processed products obtained by processing structures having the cured materials on a substrate. The processed product is fabricated by, for example, heat-drawing and punching a cured material or structure having a sheet-like form or film-like form. Examples thereof are gauges or operation panels of vehicles, office machines, electric and electronic machines, and cameras.

The substrate is not particularly limited. It can suitably be selected to a particular application. Examples thereof include paper, thread, fiber, fabrics, leather, metal, plastic, glass, wood, ceramic, or composite materials thereof. Of these, plastic substrates are preferred in terms of processability.

Moreover, the composition of the present disclosure not only forms two-dimensional texts, images, and designed coating film on various substrates, but also, for example, a cured product obtained by curing the composition and an artificial nail formed by processing a structure having the cured product over a nail or a nail-shaped plastic base material. The composition of the present disclosure is particularly suitable as a base coat for an artificial nail composition, because the composition is excellent in removability and close adhesiveness with nails.

(Artificial Nail Composition, Nail Decoration Material, and Artificial Nail)

An artificial nail composition of the present disclosure contains the composition of the present disclosure and further contains other components as needed.

Additives such as a colorant (e.g., a pigment and a dye), an inorganic filler (e.g., metal powder, calcium carbonate, talc, silica, alumina, and aluminum hydroxide), a flame retardant, an organic filler, an antioxidant, a polymerization inhibitor, a defoaming agent, a coupling agent, a leveling agent, and a rheology control agent may be blended in an appropriate amount in the artificial nail composition of the present disclosure so long as the features of the present disclosure are not spoiled.

Examples of the nail decoration material include manicures, pedicures, sculptures, and gel nails used for decoration or reinforcement of nails.

Examples of the artificial nail include a fake nail formed of a synthetic resin over a nail (real nail).

The artificial nail composition of the present disclosure is a composition to be coated over a nail of a human or an animal or over any other artificial nail and cured by light exposure, to form an artificial nail. The artificial nail formed of the artificial nail composition of the present disclosure can be removed by a removing method using, for example, an organic solvent.

An artificial nail of the present disclosure refers to a layer formed over a nail of a human or an animal or over any other artificial nail with a view to decoration or protection, or both thereof. Further, examples of the any other artificial nail include an arbitrary-shaped resin base material (fake nail) for nail decoration or protection, or both thereof.

Note that "a nail of a human and an animal, and any other artificial nail" will also be referred to simply as "a nail".

The shape of the artificial nail is not particularly limited and may be a desired shape. For example, the artificial nail may be formed in a manner to coat the surface of a nail or may be formed over a part of a nail, or with the use of, for example, a nail form, may be formed in a shape larger than a nail for nail extension.

The thickness of the artificial nail composition of the present disclosure can be controlled by coating. The thickness of the entire artificial nail is not particularly limited so long as the thickness is in a range of typical thicknesses of artificial nails, and is preferably in a range of 10 micrometers or greater but 2,000 micrometers or less in terms of durability and removability.

For example, it is common that the configuration of an artificial nail is a layer structure including any one or more selected from, for example, in order of closeness to a nail, a primer layer (a layer between the nail and a base layer for improving an adhesive force with the nail when the adhesive force is insufficient only with the base layer), a base layer (a layer between the nail and a color layer for improving the adhesive force and preventing color migration to the nail), a color layer (a layer containing a colorant), and a top layer (an outermost layer for improving durability, gloss, and aesthetic appearance). The artificial nail composition of the present disclosure can be suitably used for any of a base layer or a color layer or a top layer, or all thereof.

Above all, in view of durability and removability, it is preferable that a layer obtained by curing the artificial nail composition of the present disclosure be in contact with a nail.

Moreover, separately, a primer layer or a base layer or a color layer or a top layer, or all thereof may be provided as an upper layer of an artificial nail layer formed of the artificial nail composition of the present disclosure (the upper layer being a surface at a side of the artificial nail layer opposite to the nail) or as a lower layer (a surface between the artificial nail layer and the nail) with a view to imparting a color or gloss or close adhesiveness, or all thereof.

The artificial nail composition of the present disclosure is a photocurable artificial nail composition (also referred to as "artificial nail composition for gel nail") as a nail decoration material, and is an artificial nail composition curable by active energy rays.

<<Stored Container>>

The stored container of the present disclosure contains the composition and is suitable for the applications as described above. For example, a container that stores the composition of the present disclosure can be used as a composition cartridge or a composition bottle. Therefore, users can avoid direct contact with the composition during operations such as transfer or replacement of the composition, so that fingers and clothes are prevented from contamination. Furthermore, inclusion of foreign matters such as dust in the composition can be prevented. In addition, the container can be of any size, any form, and any material. For example, the container can be designed to a particular application. It is preferable to use a light blocking material to block the light or cover a container with a light blocking sheet, etc.

<<Image Forming Method and Forming Apparatus>>

In an image forming method of the present disclosure, a step of applying the composition of the present disclosure is not particularly limited, and examples include a coating tool such as a brush and a method for discharging the composition of the present disclosure. Examples of a curing step include active energy rays and heating. In order to cure the composition of the present disclosure with active energy rays, an irradiating step of irradiating the composition with active energy rays may be provided, an image forming apparatus of the present disclosure may include an irradiating unit configured to irradiate the composition with active energy rays and a storing part configured to store the composition of the present disclosure, and the container may be accommodated in the storing part. Further, a step of coating the composition of the present disclosure with a coating tool such as a brush and a coating unit, and a discharging step of discharging the composition of the present disclosure and a discharging unit may be provided. The discharging method is not particularly limited and examples of the discharging method include a continuous jetting method and an on-demand method. Examples of the on-demand method include a piezo method, a thermal method, and an electrostatic method.

FIG. 1 is a schematic diagram illustrating another example of the image forming apparatus (apparatus to fabricate a 3D object) of the present disclosure. An image forming apparatus 39 illustrated in FIG. 1 sequentially forms thin layers one on top of the other using a head unit having inkjet heads arranged movable in the directions indicated by the arrows A and B. In the image forming apparatus 39, an ejection head unit 30 for additive manufacturing ejects a first composition, and ejection head units 31 and 32 for support and curing these compositions eject a second composition having a different composition from the first composition, while ultraviolet irradiators 33 and 34 adjacent to the ejection head units 31 and 32 cure the compositions. To be more specific, for example, after the ejection head units 31 and 32 for support eject the second composition onto a substrate 37 for additive manufacturing and the second composition is solidified by irradiation of an active energy ray to form a first substrate layer having a pool for composition, the ejection head unit 30 for additive manufacturing ejects the first composition onto the pool followed by irradiation of an active energy ray for solidification, thereby forming a first additive manufacturing layer. This step is repeated multiple times lowering the stage 38 movable in the vertical direction to laminate the supporting layer and the additive manufacturing layer to fabricate a solid object 35. Thereafter, an additive manufacturing support 36 is removed, if desired. Although only a single ejection head unit 30 for additive manufacturing is provided to the image forming apparatus illustrated 39 in FIG. 1, it can have two or more units 30. Further, a hand or a finger may be put over the substrate 37 for additive manufacturing to form an image over a nail.

EXAMPLES

The present disclosure will be described below by way of Examples. The present disclosure should not be construed as being limited to these Examples.

<SI Value Evaluation Method>

The SI value was measured in the manner described below according a skin sensitization test by LLNA (Local Lymph Node Assay) method.

from 21 degrees C. through 25 degrees C. and a relative humidity of from 40% through 70% with ventilation of from 10 through 15 times/hour at 12-hour light-dark cycle intervals (light-on at 7 o'clock and light-out at 19 o'clock).

As the rearing cages, cages formed of polycarbonate were used. The animals used were reared 4 animals per cage.

As the feed, solid feed for test animals named MF (available from Oriental Yeast Co., Ltd.) were used. The animals used were allowed free intake of the feed. As the drinking water, the animals used were allowed free intake of tap water to which sodium hypochlorite (PURELOX, available from Oyalox Co., Ltd.) was added at a chlorine concentration of about 5 ppm through water feed bottles. As the bedding, SUN FLAKE (fir wood, power planer shavings, available from Charles River Laboratories International, Inc.) was used. The feed and rearing equipment used were sterilized in an autoclave (at 121 degrees C., for 30 minutes).

The cages and bedding were replaced at the timing of grouping and on the day of auricular lymph node extraction (when the animals were removed from the rearing room). The water feed bottles and racks were replaced at the time of grouping.

[Test Method]
<<Group Constitution>>

The group constitution used in the SI value measurement test is presented in Table 1.

TABLE 1

| Test group | Sensitizing substance | Sensitizing dose (microliter/auricle) | Number of times of sensitization | Number of animals (animal number) |
| --- | --- | --- | --- | --- |
| Medium control group | Medium only | 25 | Once/day × 3 days | 4 (1 to 4) |
| Positive control group | 2.50% HCA | 25 | Once/day × 3 days | 4 (5 to 8) |

[Test Materials]
<<Positive Control Substance>>

As a positive control substance, α-hexyl cinnamaldehyde (HCA, available from Wako Pure Chemical Industries, Ltd.) was used.

<<Medium>>

As a medium, a mixture liquid obtained by mixing acetone (available from Wako Pure Chemical Industries, Ltd.) and an olive oil (available from Fujimi Pharmaceutical Co., Ltd.) at a volume ratio (acetone:olive oil) of 4:1 was used.

<<Animals Used>>

Female mices were subjected to acclimatization for 8 days to each of the test substance, the positive control, and the medium control, including quarantine for 6 days. None of the animals were found abnormal during the quanrantine and acclimatization periods.

Using the body weights measured two days before the start of the sensitization, the animals were divided into two groups (four animals/group) in a manner that the body weight of each biont would be within ±20% of the average body weight of the population by a body weight stratified random sampling method. The animals were from 8 through 9 weeks old when the sensitization was started. Any animals that failed to be grouped were excluded from the test.

Throughout the test period, the animals used were identified by application of an oil-based ink on the tail, and cages were identified by labels.

<<Rearing Environment>>

Throughout the rearing period including the quarantine and acclimatization periods, the animals used were reared in a rearing room of a barrier system set to a temperature of

[Preparation]
<<Test Substance>>

The weighing conditions for the test substance are presented in Table 2. The test substance was weighed out in a measuring flask, and fixed to a constant volume of 1 mL with addition of a medium. The prepared liquid was put in a light-blocked airtight container (formed of glass).

TABLE 2

| | Prepared concentration (w/v %) | Amount of test substance weighed out (g) |
| --- | --- | --- |
| Test substance | 50.0 | 0.5 |

<<Positive Control Substance>>

HCA was accurately weighed out in about 0.25 g, and with addition of a medium, prepared as 1 mL of a 25.0 w/v % liquid. The prepared liquid was put in a light-blocked airtight container (formed of glass).

<<BrdU>>

5-Bromo-2'-deoxyuridine (BrdU, available from Nacalai Tesque, Inc.) was accurately weighed out in 200 mg in a measuring flask and irradiated with ultrasonic waves with addition of a saline (available from Otsuka Pharmaceutical Co., Ltd.) to be dissolved in the saline. Subsequently, the resultant was fixed to a constant volume of 20 mL and prepared as a 10 mg/mL liquid (BrdU preparation liquid). The prepared liquid was filtrated and sterilized through a sterilization filter and put in a sterilized container.

<<Preparation Timing and Storage Period>>

The positive control substance preparation liquid was prepared on the day before the sensitization was started, and stored in a cold place except during use. The medium and test substance preparation liquids were prepared on the respective days of sensitization. The BrdU liquid was prepared two days before administration, and stored in a cold place until the day of administration.

[Sensitization and BrdU administration]

<<Sensitization>>

Each of the preparation liquids of the test substance and positive control substance and the medium were applied by 25 microliters/auricle of the animals. A micropipettor was used for the application. This operation was performed once a day on three consecutive days.

<<Brdu Administration>>

About 48 hours after the final sensitization, the BrdU preparation liquid was intraperitoneally administered once in an amount of 0.5 mL per animal.

[Observation and Tests]

<<General Status>>

All of the animals used for the test were observed once or more every day from the day when the sensitization was started until the day when the auricular lymph nodes were extracted (i.e., the day when the animals were removed from the rearing room). The observation days were counted in a manner that the day when the sensitization was started was Day 1.

<<Body Weight Measurement>>

The body weight was measured on the day when the sensitization was started and on the day when the auricular lymph nodes were extracted (i.e., the day when the animals were removed from the rearing room). The average body weight and standard error were calculated per group.

<<Auricular Lymph Node Extraction and Mass Measurement>>

About 24 hours after the BrdU administration, the animals were euthanized to extract auricular lymph nodes. Surrounding tissues were removed from the extracted auricular lymph nodes and the mass of both auricular lymph nodes was measured simultaneously. The average value and standard error of the auricular lymph node weight were calculated per group. After the mass measurement, the auricular lymph nodes were cryopreserved per biont in a bio-medical freezer set to −20 degrees C.

<<Measurement of Amount of BrdU Intake>>

After returned to room temperature, the auricular lymph nodes were ground with addition of a saline and suspended in the saline. The suspension was filtrated and then dispensed into three wells per biont into a 96-well microplate, to measure the amounts of BrdU intake by an ELISA method. As the reagent, a commercially available kit (CELL PROLIFERATION ELISA, BRDU COLORIMETRIC, CAT. No. 1647229, available from Roche Diagnostics GmbH) was used. The optical densities (OD 370 nm to OD 492 nm, amounts of BrdU intake) measured with a multi-plate reader (FLUOSTAR OPTIMA, available from BMG LABTECH Inc.) from the three wells per biont were averaged as a BrdU measurement of each biont.

[Result Evaluation]

<<Calculation of Stimulation Index (SI)>>

As indicated by the formula below, the BrdU measurement of each biont was divided by the average BrdU measurement of the medium control group, to calculate the SI value of each biont. The SI value of each test group was the average of the SI values of the bionts. The SI value was rounded off at the second decimal place and expressed to the first decimal place.

$$SI = \frac{\text{Average } BrdU \text{ measurement of each biont (average or 3 wells)}}{\text{Average } BrdU \text{ measurement of medium control group (average of 4 animals)}}$$

<Constituent Components of Composition>

Abbreviations of materials and names of compounds used for composition preparation, manufacturer names, and product names are presented in Table 3-1 and Table 3-2. Monomers, which were acrylamide compounds, were synthesized in the manners described in Synthesis examples 1 to 6. Identification of the synthesized compounds was performed by a nuclear magnetic resonance spectroscopy method (instrument used: "JNM-ECX500" available from JEOL Ltd.), and purity measurement was performed by a gas chromatograph method (instrument used: "GCMS-QP2010 PLUS" available from Shimadzu Corporation). These chemical analyses were performed according to the rule.

TABLE 3-1

| | Abbrev. | Name or structure of compound | Synthesis method or manufacturer name and product |
|---|---|---|---|
| Acrylamide compound represented by general formula (1) | A1-1 | (structure) | (See Synthesis example 1) |
| | A1-2 | (structure) | (See Synthesis example 2) |
| | A1-3 | (structure) | (See Synthesis example 3) |

TABLE 3-1-continued

| | Abbrev. | Name or structure of compound | Synthesis method or manufacturer name and product |
|---|---|---|---|
| | A1-4 | [structure] | (See Synthesis example 4) |
| | A1-5 | [structure] | (See Synthesis example 5) |
| Polymerizable compound other than general formula (1) | A2-1 | [structure] | Acryloylmorpholine available from KJ Chemicals Corporation |
| | A2-2 | [structure] | 2-Hydroxyethyl mthacrylate avaiable from Tokyo Chemical Industry Co., Ltd. |

TABLE 3-2

| | Abbrev. | Name or structure of compound | Manufacturer name, product name, and molecular weight |
|---|---|---|---|
| Polymerization initiator having molecular weight of 800 or greater | B1-1 | Polyethylene glycol 200-di(β-4(4-(2-dimethylamino-2-benzyl)butanonylphenyl)piperazine) | OMNIPOL 910 available from IGM, with molecular weight of 1,032 |
| | B1-2 | 1,3-di({α-[1-chloro-9-oxo-9H-thioxanthen-4-yl)oxy] acetyl poly[oxy(1-methylethylene)]}oxy)-2,2-bis({α-[1-chloro-9-oxo-9H-thioxanthen-4-yl) oxy]acetyl poly[oxy(1-methylethylene)]}oxymethyl)propane | SPEEDCURE 7040 available from Lambson, with molecular weight of 1,899 |
| | B1-3 | Mixture of 1,3-di({α-4-(dimethylamino)benzoyl poly[oxy(1-methylethylene)]}oxy)-2,2-bis({α-4-dimethylamino)benzoyl poly[oxy(1-methyl ethylene)]} oxymethyl)propane with {α-4-(dimethylamino)benzoyl poly(oxyethylene)-poly[oxy(1-methylethylene)]-poly(oxyethylene)} 4-(dimethylamino) benzoate | SPEEDCURE 7040 available from Lambson, with molecular weight of 1,066 |
| | B1-4 | Polybutylene glycol bis(9-oxo-9H-thioxanthinyloxy) acetate | OMNIPOL TX available from IGM, with molecular weight of 820 |

TABLE 3-2-continued

| | Abbrev. | Name or structure of compound | Manufacturer name, product name, and molecular weight |
|---|---|---|---|
| | B1-5 | Oligomer of 2-hydroxy-1-(4-isopropenylphenyl)-2-methylpropan-1-one | ESACURE ONE available from IGM, with molecular weight of 1,000 or greater |
| Polymerization initiator having molecular weight of less than 800 | B2-1 | Bis(2,4,6-trimethylbenzoyl) phenyl phosphine oxide | IRGACURE 819 available from BASF Japan Ltd., with molecular weight of 418 |
| Urethane (meth)acrylate | C-1 | Structure not disclosed | CN9002 available from Tomoe Engineering Co., Ltd. |

*(C-1): urethane (meth)acrylate (available from Tomoe Engineering Co., Ltd., CN9002, with a SI value of 1.6)

Synthesis Example 1

<Synthesis of N-acryloyl-N-methyl glycine methyl ester (A1-1)>

N-methyl glycine methyl ester hydrochloride salt (available from Sigma-Aldrich Japan, reagent) (0.30 moles), potassium carbonate (available from Kanto Chemical Co., Inc., reagent) (0.45 moles), and water (400 mL) were stirred and mixed at from 0 degrees C. through 10 degrees C., and with that temperature maintained, acrylic acid chloride (available from Wako Pure Chemical Industries, Ltd., reagent) (0.33 moles) was slowly dropped to the resultant. After dropping was completed, the resultant was subjected to extraction three times with ethyl acetate (available from Kanto Chemical Co., Inc., reagent) (400 mL), and together with the ethyl acetate layer, the resultant was washed once with water (400 mL). Ethyl acetate was evaporated at a reduced pressure at 40 degrees C., to obtain the intended N-acryloyl-N-methyl glycine methyl ester (A1-1) (0.20 moles) in the form of an almost colorless, transparent liquid. The purity was 98.3% by mass.

N-acryloyl-N-methyl glycine methyl ester (A1-1) has a molecular weight of 157.2, and is a publicly known compound (CAS registration No. 72065-23-7).

Synthesis Example 2

<Synthesis of N-acryloyl-N-methyl glycine ethyl ester (A1-2)>

An intended N-acryloyl-N-methyl glycine ethyl ester (A1-2) (0.22 moles) was obtained in the form of an almost colorless, transparent liquid in the same manner as in Synthesis example 1, except that unlike in Synthesis example 1, N-methyl glycine methyl ester hydrochloride salt was changed to N-methyl glycine ethyl ester hydrochloride salt (available from Tokyo Chemical Industry Co., Ltd., reagent). The purity was 98.5% by mass.

N-acryloyl-N-methyl glycine ethyl ester (A1-2) has a molecular weight of 171.2, and is a publicly known compound (CAS registration No. 170116-05-9).

Synthesis Example 3

<Synthesis of Methacryloyloxyethyl Acrylamide (A1-3)>

N-(2-hydroxyethyl)acrylamide (available from Tokyo Chemical Industry Co., Ltd.) (13.0 g, 113 mmol) was added in dehydrated dichloromethane (70 mL). After a flask was internally purged with an argon gas, triethyl amine (17.2 g, 170 mmol) was added. After the resultant mixture was cooled to about −10 degrees C., methacrylic acid chloride (14.6 g, 140 mmol) was slowly dropped to adjust the temperature in the system to from −10 degrees C. through −5 degrees C., followed by stirring at room temperature for 2 hours. A precipitate was removed by filtration, the filtrate was washed with water, a saturated sodium bicarbonate aqueous solution, and a saturated sodium chloride aqueous solution, followed by drying with sodium sulfate and concentration at a reduced pressure, to obtain a brown oily matter.

The obtained oily matter was refined by column chromatography (WAKOGEL C300, 500 g), to obtain a colorless oily matter (13.0 g) (at a yield of about 66%).

In the manner described above, methacryloyloxyethyl acrylamide (A1-3) was synthesized.

Synthesis Example 4

<Synthesis of N-acryloyl-N-isopropylglycine isopropyl ester (A1-4)>

An intended N-acryloyl-N-isopropyl glycine isopropyl ester (A1-4) (0.22 moles) was obtained in the form of an almost colorless, transparent liquid in the same manner as in Synthesis example 1, except that unlike in Synthesis example 1, N-methyl glycine methyl ester hydrochloride salt was changed to N-isopropyl glycine isopropyl ester hydrochloride salt (available from Tokyo Chemical Industry Co., Ltd., reagent). The purity was 98.5% by mass.

N-acryloyl-N-isopropyl glycine isopropyl ester (A1-4) had a molecular weight of 213.3.

Synthesis Example 5

<Synthesis of N-acryloyl-N-methyl alanine methyl ester (A1-5)>

An intended N-acryloyl-N-methyl alanine methyl ester (A1-5) (0.22 moles) was obtained in the form of an almost colorless, transparent liquid in the same manner as in Synthesis example 1, except that unlike in Synthesis example 1, N-methyl glycine methyl ester hydrochloride salt was changed to N-methyl alanine methyl ester hydrochloride salt (available from Tokyo Chemical Industry Co., Ltd., reagent). The purity was 98.5% by mass.

N-acryloyl-N-methyl alanine methyl ester (A1-5) had a molecular weight of 171.2.

Examples 1 to 12 and Comparative Examples 1 to 4

<Production of Composition>

The components presented in Table 4 to Table 6 were mixed uniformly and filtrated through a membrane filter to remove coarse particles, to produce the compositions of Examples 1 to 12 and Comparative Examples 1 to 4.

TABLE 4

| | Abbreviation | Ex. 1 | 2 | 3 | 4 | 5 | 6 | 7 | 8 |
|---|---|---|---|---|---|---|---|---|---|
| Acrylamide compound (A1) | A1-1 | 60 | 60 | 60 | 60 | | | | |
| | A1-2 | | | | | 60 | | | |
| | A1-3 | | | | | | 60 | | |
| | A1-4 | | | | | | | 60 | |
| | A1-5 | | | | | | | | 60 |
| Polymerizable compound other than (A1) | A2-1 | | | | | | | | |
| | A2-2 | | | | | | | | |
| Polymerization initiator (B1) | B1-1 | 9 | | | | | | | |
| | B1-2 | | 4.5 | | | | | | |
| | B1-3 | | 4.5 | | | | | | |
| | B1-4 | | | 9 | | | | | |
| | B1-5 | | | | 9 | 9 | 9 | 9 | 9 |
| Polymerization initiator other than (B1) | B2-1 | | | | | | | | |
| Urethane (meth)acrylate | C-1 | 31 | 31 | 31 | 31 | 31 | 31 | 31 | 31 |
| Total (% by mass) | | 100 | 100 | 100 | 100 | 100 | 100 | 100 | 100 |

TABLE 5

| | Abbreviation | Ex. 9 | 10 | 11 | 12 |
|---|---|---|---|---|---|
| Acrylamide compound (A1) | A1-1 | 66 | 49 | 86 | 51 |
| | A1-2 | | | | |
| | A1-3 | | | | |
| | A1-4 | | | | |
| | A1-5 | | | | |
| Polymerizable compound other than (A1) | A2-1 | | | | |
| | A2-2 | | | | |
| Polymerization initiator (B1) | B1-1 | | | | |
| | B1-2 | | | | |
| | B1-3 | | | | |
| | B1-4 | | | | |
| | B1-5 | 3 | 20 | 9 | 9 |
| Polymerization initiator other than (B1) | B2-1 | | | | |
| Urethane (meth)acrylate | C-1 | 31 | 31 | 5 | 40 |
| Total (% by mass) | | 100 | 100 | 100 | 100 |

TABLE 6

| | Abbreviation | Comp. Ex. 1 | 2 | 3 | 4 |
|---|---|---|---|---|---|
| Acrylamide compound (A1) | A1-1 | 60 | | | |
| | A1-2 | | 60 | | |
| | A1-3 | | | | |
| | A1-4 | | | | |
| | A1-5 | | | | |
| Polymerizable compound other than (A1) | A2-1 | | | 60 | |
| | A2-2 | | | | 60 |
| Polymerization initiator (B1) | B1-1 | | | | |
| | B1-2 | | | | |
| | B1-3 | | | | |
| | B1-4 | | | | |
| | B1-5 | | | 9 | 9 |

TABLE 6-continued

|  | Abbreviation | Comp. Ex. | | | |
| --- | --- | --- | --- | --- | --- |
|  |  | 1 | 2 | 3 | 4 |
| Polymerization initiator other than (B1) | B2-1 | 9 | 9 |  |  |
| Urethane (meth)acrylate | C-1 | 31 | 31 | 31 | 31 |
| Total (% by mass) |  | 100 | 100 | 100 | 100 |

<Evaluation of Skin Sensitizing Potential>

The SI (Stimulation Index) values of the compositions produced in the manners described above were measured by LLNA method stipulated by, for example, OECD test guideline 429 and are presented in Table 7 and Table 8. B or A is a practically usable level.

[Evaluation criteria]
A: The SI value was less than 1.6.
B: The SI value was 1.6 or greater but 3 or less.
C: The SI value was greater than 3 but less than 6.
D: The SI value was 6 or greater.

<Evaluation of Odor>

Odor of each composition was confirmed according to the procedures (1) to (3) below, to evaluate "degree of odorlessness" according to the evaluation criteria described below. The results are presented in Table 7 and Table 8.

(1) Each composition was weighed out in an amount of about 100 mg (0.1 g) in a 50 mL sample bottle (glass bottle), and capped.

(2) The resultant was left to stand at room temperature (25 degrees C.) for 30 minutes.

(3) The nose was brought close to the sample bottle (glass bottle) to smell any odor when the bottle was uncapped.

[Evaluation Criteria]
A: No odor was felt, or an odor, if felt, was not uncomfortable.
B: A characteristic odor caused a feeling of discomfort.
C: A characteristic odor caused a strong feeling of discomfort.

TABLE 7

|  | Ex. | | | | | | | | | | | |
| --- | --- | --- | --- | --- | --- | --- | --- | --- | --- | --- | --- | --- |
|  | 1 | 2 | 3 | 4 | 5 | 6 | 7 | 8 | 9 | 10 | 11 | 12 |
| Skin sensitizing potential | A | A | A | A | A | A | B | B | A | A | A | A |
| Odor | A | A | A | A | A | A | A | A | A | A | A | A |

TABLE 8

|  | Comp. Ex. | | | |
| --- | --- | --- | --- | --- |
|  | 1 | 2 | 3 | 4 |
| Skin sensitizing potential | D | D | C | C |
| Odor | A | A | A | B |

From the results of Table 7 and Table 8, it was revealed that the compositions of Examples 1 to 12 were superior to the compositions of Comparative Examples 1 to 4 in skin sensitizing potential and odor, and would be suitably applicable as an artificial nail composition.

Aspects of the present disclosure are, for example, as follows.

<1> A composition including:
an acrylamide compound represented by general formula (1) below; urethane (meth)acrylate having a SI value of 3 or less in a skin sensitization test; and
a polymerization initiator having a molecular weight of 800 or greater,

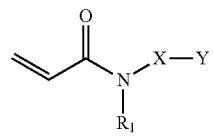

General formula (1)

where in general formula (1), $R_1$ represents an alkyl group containing 1 through 6 carbon atoms, X represents an alkylene group containing 1 through 6 carbon atoms, and Y represents any one selected from the group consisting of general formula (2) below and general formula (3) below,

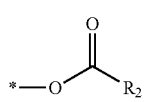

General formula (2)

where in general formula (2), $R_2$ represents an alkyl group containing 1 through 10 carbon atoms, and * represents a binding site with X above,

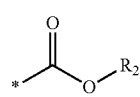

General formula (3)

where in general formula (3), $R_2$ represents an alkyl group containing 1 through 10 carbon atoms, and * represents a binding site with X above.

<2> The composition according to <1>,
wherein Y in the general formula (1) representing the acrylamide compounds is the general formula (3), and
wherein $R_2$ in the general formula (3) is an alkyl group containing 1 through 2 carbon atoms.

<3> The composition according to <1> or <2>,
wherein a content of the acrylamide compound is 30% by mass or greater but 90% by mass or less.

<4> The composition according to any one of <1> to <3>,
wherein a content of the urethane (meth)acrylate is 5% by mass or greater but 40% by mass or less.

<5> The composition according to any one of <1> to <4>,
wherein the polymerization initiator having a molecular weight of 800 or greater is at least one selected from the group consisting of polyethylene glycol 200-di(β-4(4-(2-dimethylamino-2-benzyl)butanonylphenyl)piperazine), 1,3-di({α-[1-chloro-9-oxo-9H-thioxanthen-4-yl)oxy]acetyl poly[oxy(1-methylethylene)]}oxy)-2,2-bis({α-[1-chloro-9-oxo-9H-thioxanthe n-4-yl)oxy]acetyl poly[oxy(1-methylethylene)]}oxymethyl)propane, a mixture of 1,3-di({α-4-(dimethylamino)benzoyl poly[oxy(1-methylethylene)]}oxy)-2,2-bis({α-4-(dimethylamino)benzoyl poly[oxy(1-methylethylethylene)]}oxymethyl)propane with {α-4-(dimethylamino)benzoyl poly(oxyethylene)-poly[oxy(1-methylethylene)]-poly(oxyethylene)}4-(dimethylamino)benzoate, polybutylene glycol bis(9-oxo-9H-thioxanthinyloxy) acetate, and oligomers of 2-hydroxy-1-(4-isopropenylphenyl)-2-methylpropan-1-one.

<6> The composition according to any one of <1> to <5>, wherein a content of the polymerization initiator is 1% by mass or greater but 20% by mass or less.

<7> The composition according to any one of <1> to <6>, wherein the composition is free of an organic solvent.

<8> The composition according to any one of <1> to <7>, wherein the composition is an active-energy-ray-curable composition.

<9> A stored container including:
the composition according to any one of <1> to <8>; and
a container,
wherein the composition is stored in the container.

<10> A two-dimensional or three-dimensional image forming apparatus including:
a storing part configured to store the composition according to any one of <1> to <8>;
an applying unit configured to apply the composition; and
a curing unit configured to cure the composition.

<11> The image forming apparatus according to <10>, wherein the curing unit is a UV-LED configured to emit an ultraviolet ray having a peak in a wavelength range of 365 nm or greater but 405 nm or less.

<12> A two-dimensional or three-dimensional image forming method including:
applying the composition according to any one of <1> to <8>; and curing the composition.

<13> The image forming method according to <12>, wherein the curing includes irradiating the composition with an ultraviolet ray having a peak in a wavelength range of 365 nm or greater but 405 nm or less by a UV-LED.

<14> An artificial nail composition including
the composition according to any one of <1> to <8>.

<15> A nail decoration material including
the artificial nail composition according to <14>.

<16> An artificial nail including
a cured product of the artificial nail composition according to <14>.

The composition according to any one of <1> to <8>, the stored container according to <9>, the two-dimensional or three-dimensional image forming apparatus according to <10> or <11>, the two-dimensional or three-dimensional image forming method according to <12> or <13>, the artificial nail composition according to <14>, the nail decoration material according to <15>, and the artificial nail according to <16> can solve the various problems in the related art and can achieve the object of the present disclosure.

What is claimed is:

1. A composition, comprising:
49% to 86% by mass relative to the total amount of the composition of an acrylamide compound;
urethane (meth)acrylate; and
a polymerization initiator,
wherein the composition has a Simulation Index (SI) value of 3 or less in a skin sensitization test,
wherein the polymerization initiator is at least one selected from the group consisting of polyethylene glycol 200-di(β-4(4-(2-dimethylamino-2-benzyl)butanonylphenyl)piperazine), 1,3-di({α-[1-chloro-9-oxo-9H-thioxanthen-4-yl)oxy]acetyl poly[oxy(1-methylethylene)]}oxy)-2,2-bis({α-[1-chloro-9-oxo-9H-thioxanthen-4-yl)oxy]acetyl poly[oxy(1-methylethylene)]}oxymethyl)propane, a mixture of 1,3-di({α-4-(dimethylamino)benzoyl poly[oxy(1-methylethylene)]}oxy)-2,2-bis({α-4-(dimethylamino)benzoyl poly[oxy(1-methylethylene)]}oxymethyl)propane with {α-4-(dimethylamino)benzoyl poly(oxyethylene)-poly[oxy(1-methylethylene)]-poly(oxyethylene)}4-(dimethylamino) benzoate, polybutylene glycol bis(9-oxo-9H-thioxanthinyloxy) acetate, and oligomers of 2-hydroxy-1-(4-isopropenylphenyl)-2-methylpropane-1-one,
wherein the acrylamide compound is selected from acrylamides A1-1 to A1-5

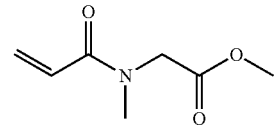
A1-1

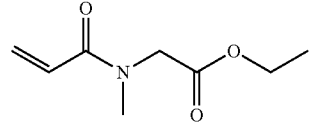
A1-2

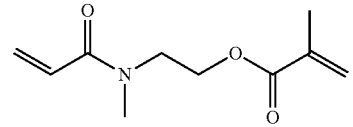
A1-3

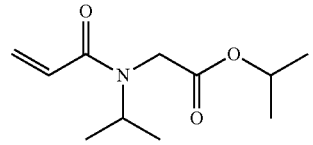
A1-4

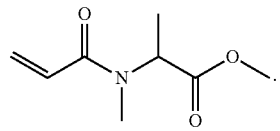
A1-5

2. The composition according to claim 1,
wherein the acrylamide compound is A1-1.

3. The composition according to claim 1,
wherein a content of the urethane (meth)acrylate is 5% by mass to 40% by mass based on the total amount of the composition.

4. The composition according to claim 1,
wherein a content of the polymerization initiator is 1% by mass to 20% by mass based on the total amount of the composition.

5. The composition according to claim 1,
wherein the composition is an active-energy-ray-curable composition.

6. A stored container, comprising:
the composition according to claim 1; and
a container,
wherein the composition is stored in the container.

7. A two-dimensional or three-dimensional image forming apparatus, comprising:
a storing part which comprises a composition;
an applying unit configured to apply the composition; and
a curing unit configured to cure the composition, wherein the composition comprises a composition according to claim 1.

8. A two-dimensional or three-dimensional image forming method, comprising:
applying a composition; and
curing the composition,
wherein the composition comprises a composition according to claim 1.

9. An artificial nail composition, comprising the composition according to claim 1.

10. A nail decoration material, comprising the artificial nail composition according to claim 9.

11. An artificial nail, comprising a cured product of the artificial nail composition according to claim 9.

12. The composition according to claim 1, wherein the polymerization initiator is at least one selected from the group consisting of polyethylene glycol 200-di(β-4(4-(2-dimethylamino-2-benzyl)butanonylphenyl)piperazine), 1,3-di({α-[1-chloro-9-oxo-9H-thioxanthen-4-yl)oxy]acetyl poly[oxy(1-methylethylene)]}oxy)-2,2-bis({α-[1-chloro-9-oxo-9H-thioxanthen-4-yl)oxy]acetyl poly[oxy(1-methylethylene)]}oxymethyl)propane, a mixture of 1,3-di({α-4-(dimethylamino)benzoyl poly[oxy(1-methylethylene)]}oxy)-2,2-bis({α-4-(dimethylamino)benzoyl poly[oxy(1-methylethylene)]}oxymethyl)propane with {α-4-(dimethylamino)benzoyl poly(oxyethylene)-poly[oxy(1-methylethylene)]-poly(oxyethylene)}4-(dimethylamino) benzoate, and polybutylene glycol bis(9-oxo-9H-thioxanthinyloxy) acetate.

13. The composition according to claim 1, wherein the acrylamide compound is selected from acrylamides A1-2 to A1-5.

14. The composition according to claim 1, wherein the composition comprises 10-40% of the urethane (meth)acrylate, and 5-10% of the initiator.

15. The composition according to claim 1, which comprises 3-20% of the initiator, and 5-40% of the urethane (meth)acrylate.

16. The composition according to claim 1, which consists essentially of the acrylamide, urethane (meth)acrylate, and initiator.

17. The composition according to claim 2, wherein the composition comprises 10-40% of the urethane (meth)acrylate, and 5-10% of the initiator.

18. The composition according to claim 17, which consists essentially of the acrylamide, urethane (meth)acrylate, and initiator.

19. An artificial nail comprising a cured product of the composition according to claim 18.

* * * * *